(12) United States Patent
Amundson

(10) Patent No.: US 10,467,699 B2
(45) Date of Patent: Nov. 5, 2019

(54) SYSTEM AND METHOD FOR CONVEYING AND PROCESSING PERSONAL HEALTH INFORMATION

(76) Inventor: Russell Henry Amundson, Merion Station, PA (US)

(*) Notice: Subject to any disclaimer, the term of this patent is extended or adjusted under 35 U.S.C. 154(b) by 1310 days.

(21) Appl. No.: 13/094,443

(22) Filed: Apr. 26, 2011

(65) Prior Publication Data
US 2012/0278093 A1 Nov. 1, 2012

(51) Int. Cl.
*G06Q 50/00* (2012.01)
*G06Q 40/08* (2012.01)
*G06Q 50/22* (2018.01)
*G06Q 10/00* (2012.01)

(52) U.S. Cl.
CPC .............. *G06Q 40/08* (2013.01); *G06Q 50/22* (2013.01)

(58) Field of Classification Search
CPC .. G06F 19/322; G06F 19/3487; G06F 19/345; G06F 19/3462; G06F 17/243
USPC ........................................................ 705/2–3
See application file for complete search history.

(56) References Cited

U.S. PATENT DOCUMENTS

| | | | | |
|---|---|---|---|---|
| 6,505,218 B2 * | 1/2003 | Umen et al. | | 715/236 |
| 7,689,437 B1 * | 3/2010 | Teller et al. | | 705/2 |
| 2001/0041991 A1 * | 11/2001 | Segal et al. | | 705/3 |
| 2002/0133378 A1 * | 9/2002 | Mault et al. | | 705/3 |
| 2003/0140044 A1 * | 7/2003 | Mok et al. | | 707/10 |
| 2011/0040578 A1 * | 2/2011 | Ramsey | | 705/3 |

* cited by examiner

*Primary Examiner* — Tran N Nguyen
(74) *Attorney, Agent, or Firm* — Sterne, Kessler, Goldstein & Fox P.L.L.C.

(57) ABSTRACT

Approaches for converting analog health information to a digital database are described. Worksheets comprising questions for a patient are displayed in an interface that can be used to review and edit responses. A system receives responses to the questions, displays the responses, and sends the responses to a healthcare provider. The system includes a provider interface that can be used to annotate and edit worksheet data. The system converts and declares a worksheet as a medical record for the patient. The system securely stores worksheet data and medical records and receives a selection of a subset of this information. The system grants access to the subset of information to designated entities. The system concisely presents health information for analysis and workflow improvement. The system receives login credentials, determines a login type, and displays an interface based upon the login type. The system securely transmits personal health information to designated entities.

28 Claims, 30 Drawing Sheets

BASIC WORKFLOW

WORKSHEETS/EXAM WORKSHEETS

Create a data field e.g. 10 worksheets.

Each worksheet 10 questions

Each question up to 10 answers 10 x 10 x 10

Each "pixel" is a data point.

Each data point is "tagged" for several criteria.

1) Reviewed and/or examined

Not reviewed or examined

If done, i.e., reviewed and/or examined provides a tally report, which determines "level of service", and appropriate billing level.

(i.e., codes for levels 1-5)

2) Normal/abnormal

Summary of abnormal generally constitutes a "clinical report" - This also allows for grid/grid comparison/connection for SOS 3) Body system Summary of "abnormals", segregated by body system, allows for Spectral Array report.

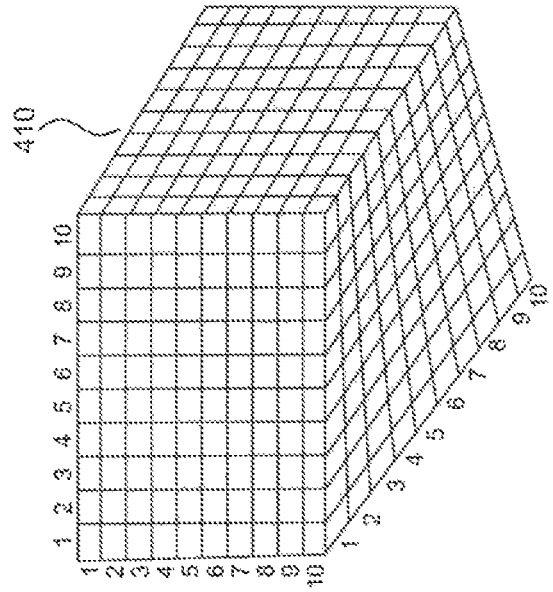

FIG. 4

Type of data —— 505
1 – patient subjective complaint
2 – history element
3 – exam element
4 – ancillary data element
5 – procedure element
6 – surgery element This weighs the data element referable to each body system. The scale is one of increasing objectivity and level of intervention. There is no reason why- in addition to to body system specific color coding each pixel is not level of severity (1-6) coded. Each line of pixels represents a timeline of contiguous encounters.

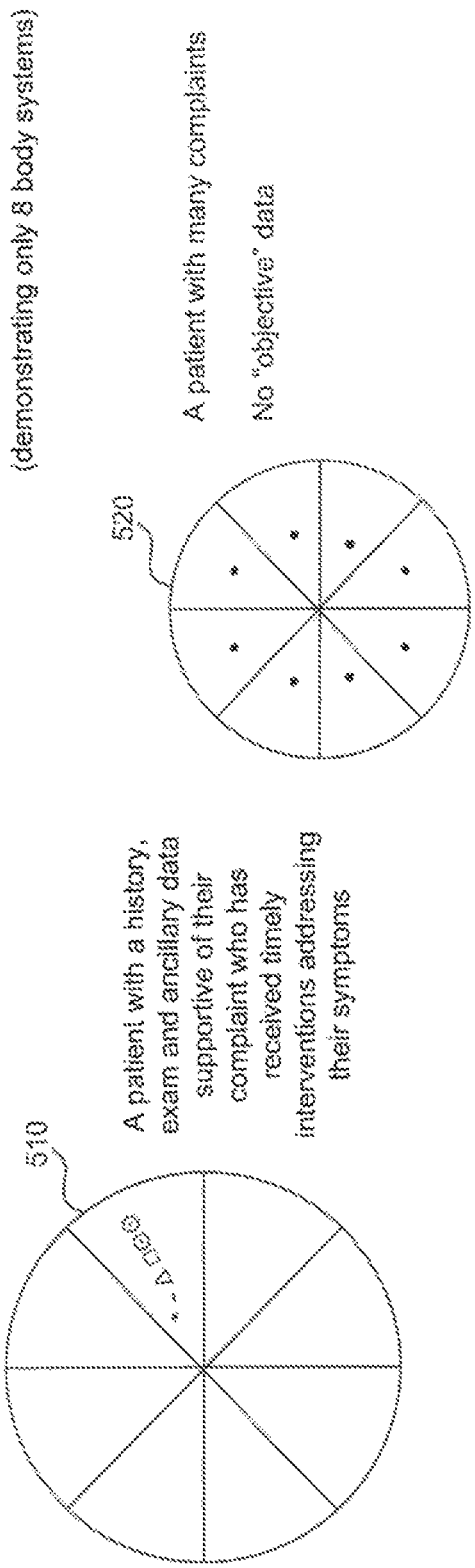

(demonstrating only 8 body systems)

A patient with many complaints

No "objective" data

A patient with a history, exam and ancillary data supportive of their complaint who has received timely interventions addressing their symptoms

SOS

The grid is connected to a diagnosis.

The grid, in our example is a digital code.

Worksheet 1
Question 1
Answer 6
Might look like   [1.1.000001 0000]
   or   [1.1.f]
   or   [a.a.f]
   or
1st worksheet
1st question
6th answer
615
410

It is much quicker/accurate to review digital format for correlations between data and diagnosis.

1 – Accuracy and diagnosis – (SOS)
2 – Does or will third party approve payment and service?

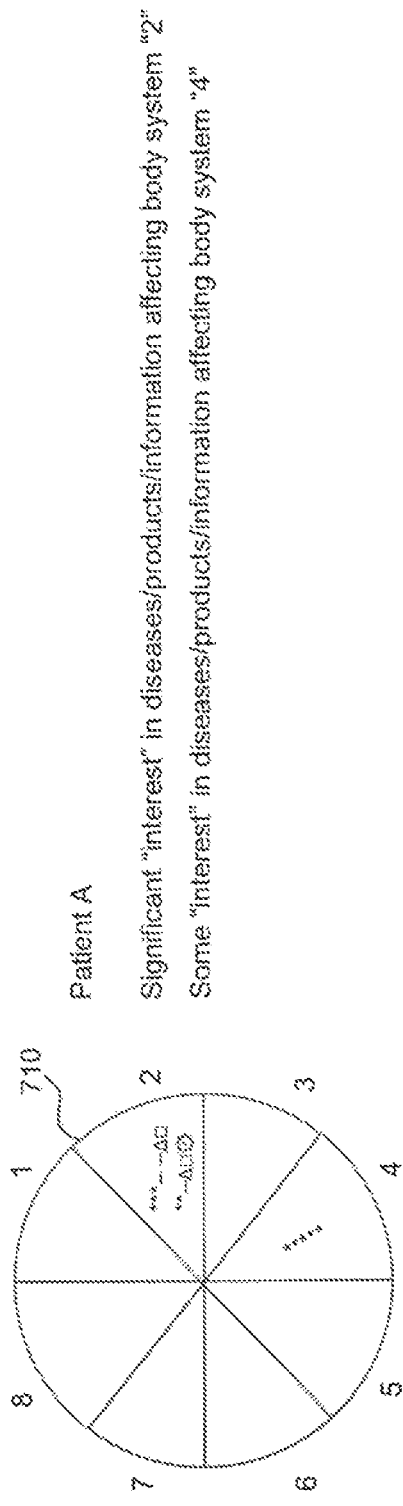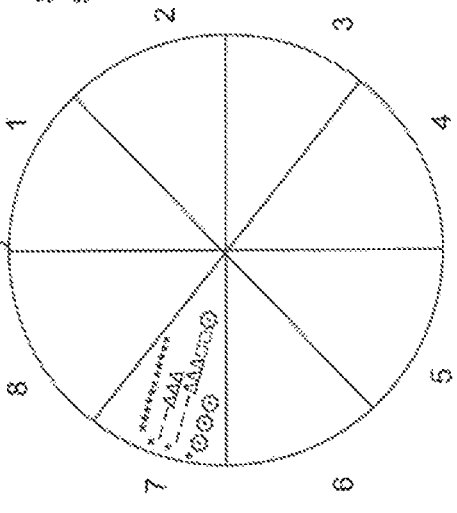
FIG. 7

Sign In Authorization Levels SINAL    1000

| | | | | |
|---|---|---|---|---|
| Access Web Site | Secure Log in as patient, provider or administrator | Data entry via worksheets by user, either patient or provider | Secure storage of data with HIPAA compliant mechanism | Ability to grant access to data to provider by patient, or provider to provider | 1010 |
| Access Web Site | Secure log in as provider | Worksheet review, annotation and correction; Submission as record; Data entry via worksheets | Documentation now recorded as medical record and stored securely | Ability to grant access to record to downstream providers and third party entities | 1020 |
| Access Web Site | Secure log in as administrator | Edit, modify and format worksheets, records and reports; Data entry via worksheets | Determine access to data, records and reports to providers | Ability to grant access to third party entities | 1030 |
| Super Administrator | Contract for customization services | Contract for scheduling services; Data entry via worksheets | Contract for diagnosis substantiation services | Contract for educational and information distribution services | 1040 |

SYSTEM AND METHOD FOR CONVEYING AND PROCESSING PERSONAL HEALTH INFORMATION

BACKGROUND OF THE INVENTION

Field of the Invention

The present invention relates to health information and, more particularly to displaying and editing health information using mobile client devices.

Background of the Invention

Healthcare providers, insurers, pharmacies, and other organizations have a variety of facilities to enable them to obtain, view, and maintain medical records and other health information. With the advent of computers, relational database management systems (RDBMSs), the Internet, and wireless communication devices, information that was once stored in physical files in paper form or in central database servers only available to organizations that "owned" or maintained the data can now be made available to patients and authenticated third parties via a variety of client computing devices, such as, but not limited to mobile client devices.

Despite the ability of providers and patients to view portions of a patients medical information from a computer having an Internet connection, users of mobile devices often find they need medical information when a wireless Internet connection is unavailable. Whether at a provider's office or facility such as a hospital, clinic, lab, or pharmacy, patients currently depend on another entity to access their medical information.

Mobile devices are in common usage, many featuring powerful processors, larger and more colorful displays, and wireless networking capabilities. Despite these advances in mobile technology, as compared to desktop and laptop computers, mobile devices typically have greater limitations on memory capacity, data storage capacity, central processing unit (CPU) capabilities, and networkability. Given the versatility of mobile devices, it is desirable to implement means by which these mobile devices can interact with servers to maintain and display account data in the context of potentially intermittent, unreliable, occasionally-connected, or temporarily-unavailable networking capabilities.

Advancement in mobile devices such as mobile phones, personal digital assistants (PDAs), smart phones, hand held computers, palmtop computers, ultra-mobile personal computers (PCs), devices operating according to the MICROSOFT™ Pocket PC specification with the MICROSOFT™ WINDOWS™ CE operating system (OS), devices running the ANDROID™ OS, devices running the Symbian OS, devices running the PALM™ OS, devices running the webOS by Hewlett Packard, Inc. of Palo Alto, Calif. devices running the Apple IPHONE™ OS by Apple Computer, Inc. of Cupertino, Calif., mobile phones, BLACKBERRY™ devices by Research In Motion of Waterloo, Ontario, Canada, and devices capable of running mobile browsers such as INTERNET EXPLORER™ (IE) Mobile have made mobile Internet connections possible without laptop, notebook, netbook or tablet computers. However, the limited screen size and computing power of these devices also limits the capabilities of the Internet browsers installed on these devices. As a result, these devices are often unable to display complicated web content and unable to comply with the rigorous Internet security measures employed by medical-related websites, such as health insurance and healthcare provider websites.

Internet browsers such as IE, Firefox, Chrome, and Safari can save the information they download so that a web page can be viewed later without an active Internet connection. Internet browsers for mobile and non-mobile platforms can save and synchronize Internet web pages. However, current web browsers are not typically configured to selectively store certain information nor do they have the ability to protect sensitive health information that would be necessarily stored in saving the contents of the web page. As a result, most web browsers simply store copies of viewed web pages for a certain amount of time. To avoid congesting a computer with cached data, web browsers often set a limit on how much data will be saved. Using a web browser's cache may provide offline content in certain circumstances, but not in others. When a web page to be saved features dynamic or scripted information, an Internet browser will only save the last viewed screen. For example, a Uniform Resource Locator (URL) address for the website for accessing a web-based email client such as GOOGLE™ GMAIL™ is typically static. However, the information displayed on the web page changes dynamically as email is added and deleted from the inbox of the email account. As a result, relying on an Internet's browser cache to view health information accessed or edited two weeks ago is ineffective.

An additional shortcoming of the browser-cache model for viewing health information is that web controls cannot be used to vary the display or content of the page. For example, if a user of an insurance website wants to view all the claims that have been processed in a given time period such as the past month or year, a user could use the insurer's website to download this information, provided the user has an active Internet connection. Without an active Internet connection, the user could view any cached pages on his computer, but these pages will not provide this particular set of information in cases where the medical information (i.e., processed claims) has changed since the pages were cached. Additionally, most current web browsers do not store, in cache, pages that have been encrypted. This step is taken to prevent other users and programs from browsing through a user's web cache for sensitive, private health information. Additionally, personal health information is often encrypted or otherwise secured in order to comply with the Health Insurance Portability and Accountability Act (HIPAA) of 1996 (P.L.104-191). However, current mobile data delivery techniques cannot display editable personal health information in a HIPAA-compliant manner without resulting in degraded response times, which can result in connections that timeout and/or are terminated before medical data requests from a mobile device can be fulfilled.

Accordingly, what is desired is a means of securely providing medical information to registered patients and providers via mobile devices. What is further desired are methods, systems, and devices for accessing and viewing medical information on mobile devices.

What is needed are mobile client devices configured to reduce inefficient, redundant medical data entry and to facilitate secure transmission and retrieval of medical data. What is further needed are mobile client devices configured to reduce error rates in medical data entry and improve work flow for processing medical data, thereby saving time and expense.

SUMMARY OF THE INVENTION

The present invention includes methods, devices, and systems for processing and conveying medical data. More specifically, embodiments of the present invention convert large amounts of analog information into a standardized digital presentation, which can be consistently and concisely presented in graphical form and subsequently used for analysis and comparison. Methods, systems, and computer program products described herein accomplish this by means of interactive worksheets, standards of substantiation (SOS), spectral array and a graphical user interface (GUI). An SOS report is employed as part of a workflow solution that reduces inefficiencies associated with traditional medical records work flow and analog data analysis. The spectral array described herein can be used for research, marketing and distribution of relevant educational information based on a patient's body system "data density" instead of personally identifiable data.

Embodiments of the invention convert a complex analog information set to a digital database that is concisely presented graphically for analysis and workflow improvement. Such workflow improvement provides increased efficiency and improved data accuracy through converting/digitizing analog worksheet data. Embodiments of the invention enable configuration and mapping of analog information into digital data, which in turn reduces need for human users to analyze information to substantiate medical diagnoses, insurance claims, and medical procedures requested. In this way, embodiments of the invention provide systems and methods that improve efficiency, data accuracy, and reduce cost, redundancy and inaccuracy of health care delivery.

When using the present invention, registered patients and providers can view personal medical information live while connected to the Internet. If no Internet connection is available, the patients and providers can view the personal health information offline. Viewing an offline web page is supported by Internet browsers such as MICROSOFT™ INTERNET EXPLORER™ (IE), IE Mobile, Mozilla Firefox, GOOGLE™ Chrome, and Apple Safari.

Embodiments of the invention convey medical information such as responses to worksheet questionnaires between a mobile device and a computing device used to store the worksheet data as a medical record and make the information available to authenticated patients, providers, and administrators. In embodiments of the invention, the medical data may be displayed in a user interface displaying a worksheet comprising a plurality of questions for a registered patient. The methods, devices and systems may provide a patient with access to his or her medical information by collecting the information at a server that can receive information from providers and administrators. Additionally, methods for downloading and displaying interactive worksheets for collecting the medical information on the client are disclosed. Also, specialized software for converting the worksheet data received from the client into a medical record is disclosed. According to embodiments of the invention, software may display medical records graphically to aid in arriving at more accurate diagnoses. The software may also contain routines that allow the server to determine if it has any additional medical records associated with a particular patient in order to aid in spectral array analysis of the patient's condition. The software may comprise encryption routines to protect the privacy of patients medical records and worksheet data. For example, such encryption routines may be HIPAA-compliant 32-bit encryption routines. Additionally, the software may comprise a special access password feature, which allows a second user to view or modify the first user's medical information. Also, the software may contain a privileged access routine that allows the first user to enable an option in the second user's account to view or modify the first user's medical information.

For example, in accordance with an embodiment of the present invention, an electronic information system provides medical information to a user. The system may comprise a server having a database and a client. The server may comprise software having: a reception routine comprising instructions to cause the server to receive personal health information; a storage routine comprising instructions to cause the server to store the personal health information in the server; a selection routine comprising instructions for causing the server to select a subset of the medical information stored by the storage routine; and an output routine comprising instructions for causing the server to send the subset of the medical information to the client. The mobile client device may comprise software having: a reception routine comprising instructions for causing the client to receive the medical information from the server; a storage routine comprising instructions to cause the client to store the information locally in the mobile client device; and a display routine comprising instructions for causing the client to display the medical information received by the client device's reception routine.

In an embodiment, a user, such as, but not limited to a registered patient or a healthcare provider, enters data into a plurality of worksheets. This worksheet data can be securely stored and transmitted to one or more designated entities, such as, but not limited to downstream providers (i.e., pharmacies), medical insurers, attorneys, and other third parties. According to an embodiment, both exam worksheet data and other types of worksheet data, can be viewed, edited, corrected, annotated and converted into a medical record by healthcare providers. The medical record can be securely stored and transmitted. In an embodiment, both worksheet data and medical records are securely stored for subsequent transmission to designated entities. In one embodiment, healthcare providers enter, edit, and annotate exam worksheets and other types of worksheets in conjunction with a patient interaction which may include an exam and history taking episode. According to an embodiment, exam worksheet data can be viewed, but not edited by patient users.

In accordance with embodiments of the invention, a plurality of worksheets are available to patient users. These worksheets include, but are not limited to: chief complaint worksheets, history of present illness worksheets, accident worksheets, collision worksheets, allergy worksheets, medication worksheets, past medical history worksheets, surgery worksheets, family history worksheets, social history worksheets and review of systems worksheets. In an embodiment, these worksheets are also available to healthcare providers. According to an embodiment, an improved workflow process comprising SOS utilizes the worksheets to reduce analog data to digital grids. The process allows for point of service to point of service comparison between healthcare providers, groups and networks.

In an embodiment, a spectral array is presented as a graphic image. One advantage of the spectral array is that it reduces complex medical histories to a body system coded display comprising color, symbol and timeline elements to convey a patient's entire medical 'story' as an easily decipherable image. Another advantage of displaying spectral arrays is that they enable patient education directed links (PEDLs), which, in an embodiment, comprise directed educational links relevant to a registered patient based upon their body system specific ailments and reported complaints.

An embodiment of the invention includes a method for determining a diagnosis, requesting a procedure or intervention, and certification of appropriate correspondence between the worksheet data, which may include history, exam and ancillary data, the diagnosis and the procedure. A mobile client device improves this method by conveying worksheets, medical records, reports and other data as described herein.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant arts) based on the teachings contained herein.

BRIEF DESCRIPTION OF THE DRAWINGS/FIGURES

FIG. 4 depicts a medical exam worksheet workflow, in accordance with an embodiment of the present invention.

FIG. 5 illustrates mapping of worksheet elements to body systems, in accordance with an embodiment of the present invention.

FIG. 7 shows an exemplary embodiment of how worksheet data is used for spectral array analysis.

FIG. 10 depicts sign in authorization levels (SINAL) and their privileges, in accordance with an embodiment of the present invention.

FIGS. 13-29 depict a graphical user interface (GUI) for an electronic information system that displays interactive medical exam worksheets, medical records, and analysis/diagnosis tools, according to an embodiment of the invention.

DETAILED DESCRIPTION

Figure 1:
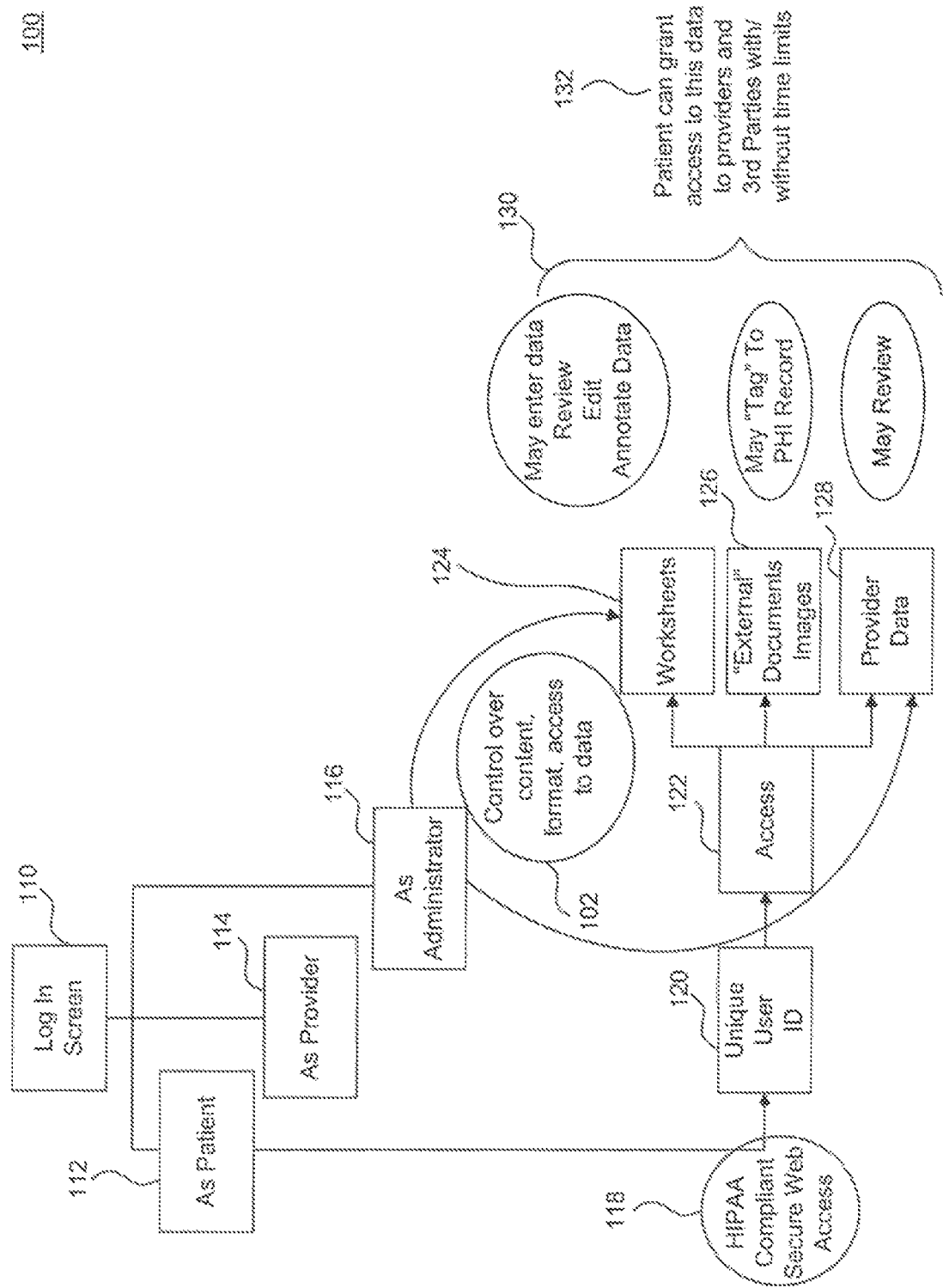
FIG. 1 illustrates a health information system wherein patients can access, enter, edit, and grant access to medical information, in accordance with an embodiment of the present invention.

Embodiments relate to methods and systems for displaying, searching and editing personal health information. While the present invention is described herein with reference to illustrative embodiments for particular applications, it should be understood that embodiments are not limited thereto. Other embodiments are possible, and modifications can be made to the embodiments within the spirit and scope of the teachings herein and additional fields in which the embodiments would be of significant utility. Further, when a particular feature, structure, or characteristic is described in connection with an embodiment, it is submitted that it is within the knowledge of one skilled in the relevant art to effect such feature, structure, or characteristic in connection with other embodiments whether or not explicitly described.

It would also be apparent to one of skill in the relevant art that the embodiments, as described herein, can be implemented in many different embodiments of software, hardware, firmware, and/or the entities illustrated in the figures. Any actual software code with the specialized control of hardware to implement embodiments is not limiting of the detailed description. Thus, the operational behavior of embodiments will be described with the understanding that modifications and variations of the embodiments are possible, given the level of detail presented herein.

In the detailed description herein, references to "one embodiment," "an embodiment," "example embodiment" etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Definitions

As used herein, a personal health record (PHR) is any collection of medical data that is maintained by an individual or an organization on behalf of an individual or a selected subset of that data. A PHR may be a collection of medical history data pertaining to an individual user that is collected and maintained by healthcare providers, insurers, and government organizations. A PHR may provide a complete and accurate summary of the health and medical history of an individual by gathering data from many sources, including, but not limited to hospitals, physicians, pharmacies, assisted living facilities, medical clinics, and health insurance companies. An individual PHR can contain a diverse range of data, including medical insurance information. A PHR may include information about one or more of: an individual's allergies and adverse drug reactions; medications prescribed to the individual—including past and current prescriptions, dosage, frequency, related prescriptions, interactions with other drugs and foods, side effects, doses, dosage schedule, and remaining refills; over the counter medication history—including past and present medications and herbal remedies obtained from pharmacies, clinics, and online providers; the individual's illnesses and hospitalization history; surgeries and other procedures performed on the individual; the individual's vaccination history; laboratory test results for the individual—including but not limited to blood analysis, urinalysis, drug tests, biopsies; any clinical trials the individual has participated in; psychological evaluations; and the individual's family medical history. Information stored in a PHR may be used to check for potential/future prescriptions and procedures (i.e., drug-drug interaction checking or electronic messaging between patients and providers regarding potential issues related to a scheduled procedure). Information stored in a PHR may be used to send messages tailored to an individual. These messages may include, but are not limited to information related to the individual's current or past illnesses, reminders for healthcare appointments, reminders to refill prescriptions, and reminders to take medication. PHR data may be hosted by a third party and accessible via a client, A PHR may be maintained by an individual via a client connected to a server where the PHR is securely stored.

As used throughout the following detailed description, a terminal and a personal computer (PC) may have the same hardware and be connected to the same type of network structure. A terminal and PC may comprise single computing devices. For example, a PC may be a commercially available personal computer with one or more central processing units (CPUs). Alternatively, a PC may comprise multiple computing devices and/or computing functionality hosted on one or more servers (i.e., in a collection of servers such as a server cluster or server farm). However, to facilitate the explanation of the present invention, a terminal shall refer to a public or semi-public, generic computer such as a library computer, school computer, or Internet cafe computer. A terminal is designed to receive medical information from a server or a web server, and may have terminal software installed in the memory of the terminal. As used herein, the term PC shall refer to a private or semi-private, generic computer such a personal computer or a laptop.

As used herein, the term "server" encompasses computing devices that are designed to function as one or more of application servers, database servers, file servers, key servers, web servers, and fax servers. A server may be comprised of one or more server machines. A server may be implemented as collection of servers such as a server farm or server cluster. For example, a server and web server may be commercially available server machines with one or more central processing units (CPUs). Alternatively, these servers may comprise multiple computing devices and/or computing functionality hosted on multiple server machines (i.e., a server farm).

As used herein, the term "processor" is any electronic circuit that can execute computer instructions or programs. A processor may comprise one or more central processing units (CPUs). A processor may be implemented as multiple processors and their interconnections on a single silicon chip (i.e., a multi-core microprocessor).

In embodiments, a PC, client, terminal, server, and a mobile device may all comprise similar software running on the indicated hardware. However, in most instances a specially adapted version of the software will be installed on each of these types of computing devices. For example, a terminal may have terminal software, a PC may have PC software, and a server may have server software.

Figure 30:
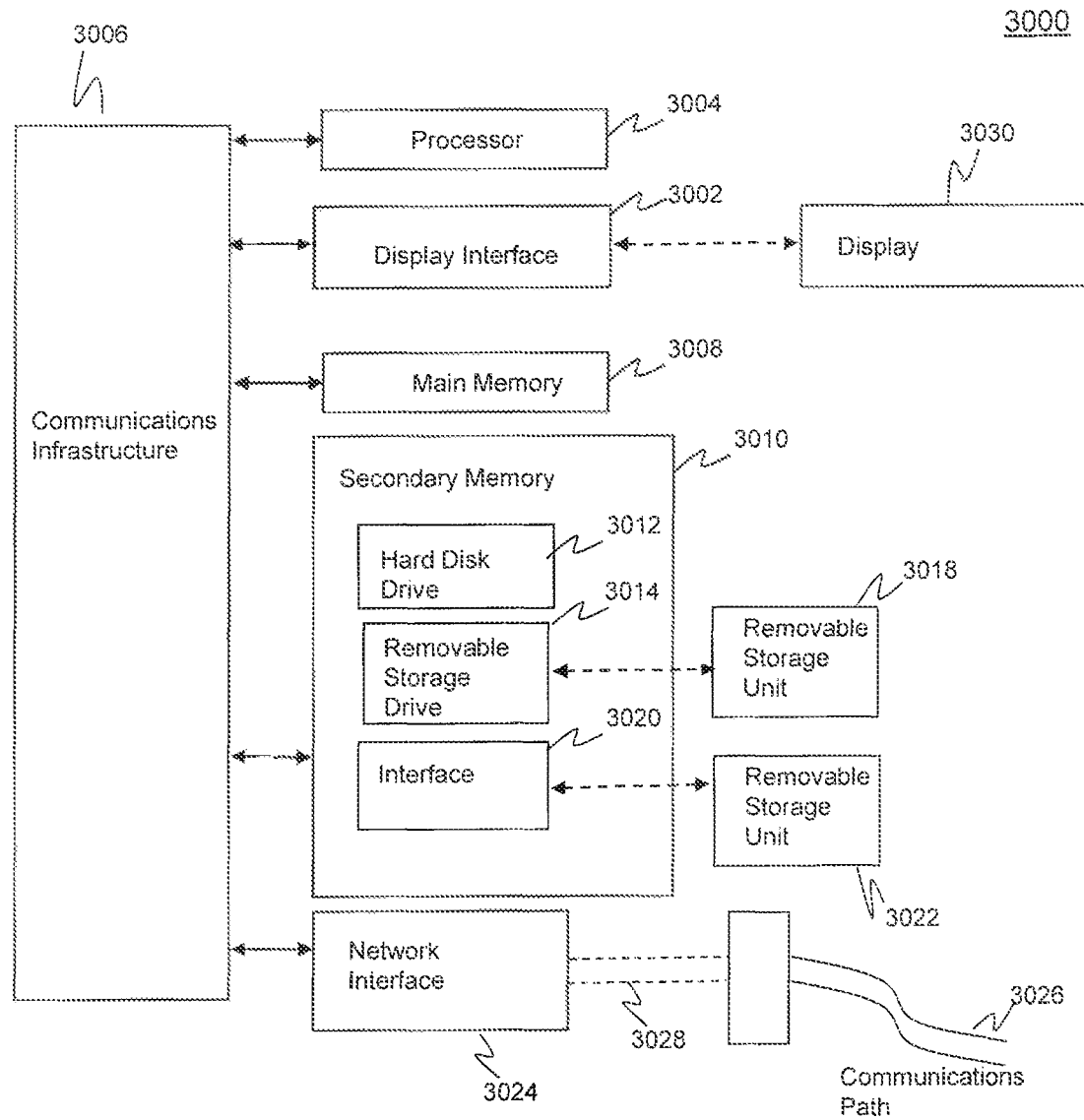
FIG. 30 depicts an example computer system in which the present invention may be implemented.

As used herein, the terms "computer" and "computing device" (a computer is shown in FIG. 30) encompass PCs, terminals, and other clients that are designed to receive information from or transmit information to a server or a web server. PCs, terminals, and mobile devices are referred to generally as clients. A user's computer used in an office or place of business may be classified as either a PC or a terminal depending on the level of access and the type of software installed.

Unless specifically stated differently, a user is interchangeably used herein to identify a human patient (i.e., a human user), a software agent, or a group of users and/or software agents. Besides a human user who needs to access medical information, a software application or agent sometimes needs to access medical and insurance information. Accordingly, unless specifically stated, the term "user" as used herein does not necessarily pertain to a human being.

As used herein, insurance information refers to any type of insurance information. In embodiments of the invention, insurance information can be, but is not limited to, medical insurance, life insurance, supplemental income protection insurance, auto/collision insurance, property insurance, disability insurance, and workman's compensation insurance. Such insurance information may be related to an injury claim, medical claims, or other occurrences related to medical information where the payer (insurer) may be one or more of a medical, collision (i.e., auto policy), property (i.e., homeowner policy), and workman's compensation insurance carriers. Medical insurance may be, but is not limited to dental insurance, vision insurance, Medicare, Medicaid, and health insurance.

As used herein, in an embodiment, a mobile device may be any wireless mobile computing or communication device such as a mobile phone, a personal digital assistant (PDA), a smart phone, a hand held computer, a palmtop computer, an ultra-mobile PC, a device operating according to the MICROSOFT™ Pocket PC specification with the MICROSOFT™ WINDOWS™ CE operating system (OS), a device running the Symbian OS, a device running the WINDOWS™ Mobile OS, a device running the WINDOWS™ Phone OS, a device running the GOOGLE™ Android OS, a device running the PALM™ OS, a BLACKBERRY™ device, a TREO™, or a device running an Apple IPHONE™ OS. Mobile device connection maintenance software may be downloaded from a remote web server and installed through an installation routine or installed in response to a Short Message Service (SMS) message and hyperlink sent to the mobile device. Alternatively, a version of the mobile device worksheet software corresponding to a specific mobile device (i.e., make, model, operating system, and browser) may be pushed to the mobile device from a download server based on mobile device information contained within HTTP header data in an HTTP request sent from the mobile device.

Finally, a user and a provider can be distinguished. A user is a person, organization, business or other legal entity that uses the system to view, obtain, modify, or distribute medical and insurance information. Insurance information can comprise one or more of medical insurance information, collision insurance information, property insurance information, and workman's compensation insurance information. Such insurance information may be related to an injury claim, medical claims, or other occurrences related to medical information where the payer (insurer) may be one or more of a medical, collision (i.e., auto policy), property (i.e., homeowner policy), and workman's compensation insurance carriers. A provider is a person, organization, business or other legal entity that provides medical care to a patient. Providers can include persons or organizations involved in providing nursing home care or assisted living care as well as pharmaceutical intervention medical care. Providers or their agents may add information or modify the information in a patient's medical history. Both users and providers may add, update, and view information in the system.

System Embodiments

Figure 2:
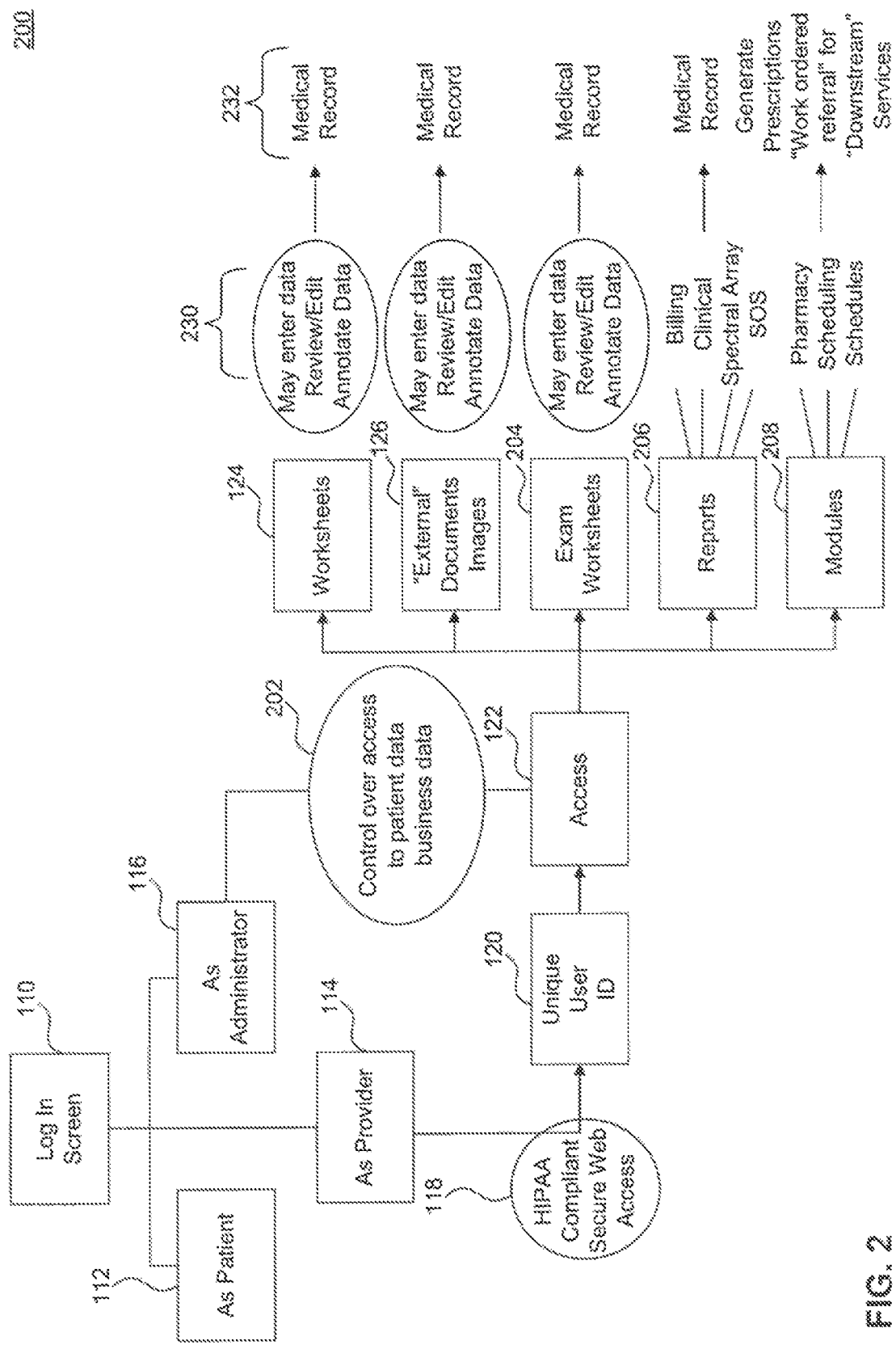
FIG. 2 illustrates a health information system Wherein providers can access, enter, edit, annotate, and review medical information, in accordance with an embodiment of the present invention.
Figure 3:
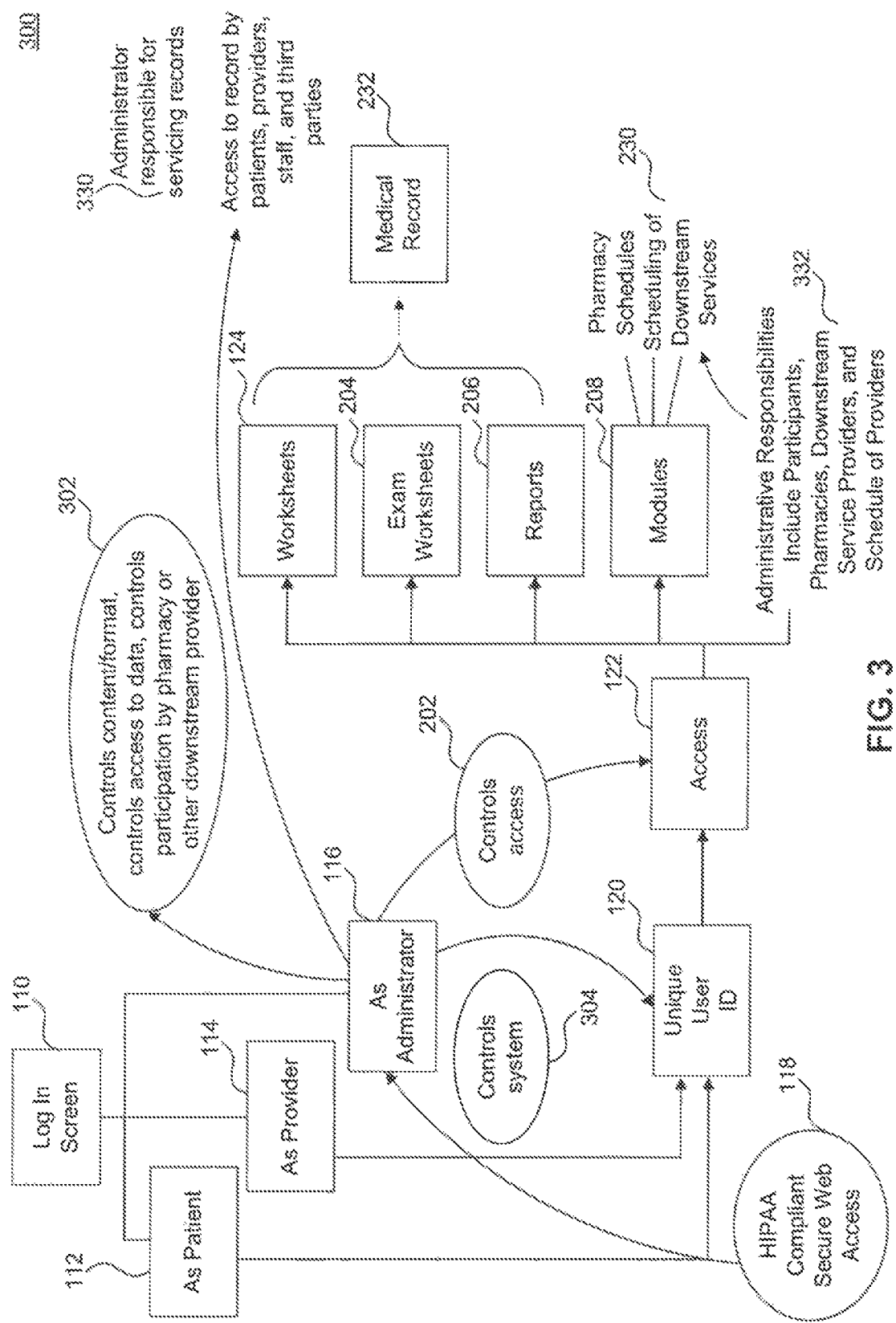
FIG. 3 illustrates a health information system wherein administrators can access, format, control access to and control content of medical information, in accordance with an embodiment of the present invention.

Personal health information systems 100-300 are illustrated in FIGS. 1-3, which are described in the following paragraphs.

As shown in FIG. 1, a plurality of login types can be detected by log in screen 110. The login types may include, but are not limited to, patient 112, provider 114, and administrator 116. As shown in FIG. 1, in an embodiment, upon detecting a login by an administrator 116, administrator privileges 102 can be granted to control content, format medical data, and to access medical data. In embodiments of the invention, depending upon the type of class of administrator 116, administrator privileges may include either administrator privileges 1030 or super administrator privileges 1040, as described in detail below with reference to FIG. 10.

Alternatively, upon detecting a login by a patient 112, access is granted, via a HIPAA compliant secure web site 118 to medical data. As shown in FIG. 1, based upon a unique user ID 120, patient privileges (i.e., access) 122 are granted to one or more of worksheets 124, external documents and images 126, and provider data 128. External documents and images 126 can include data from outside secure website 118 that can be uploaded to the site and "tagged" by the unique identifier associated with the patient 112 as data belonging to patient 112. In accordance with an embodiment of the invention, administrators 116, providers 120, and patients 112 may be granted privileges 130 to enter, review, edit, and annotate data. Privileges 130 can also include permissions to "tag" and review personal health information (PHI) records, including external documents and images 126 from outside secure website 118. Patients 112 can also grant third party privileges 132 to providers and other third parties. As illustrated in FIG. 1, third party privileges 132 can be granted on either a temporary or permanent basis (i.e., with or without time limits or expiration dates).

In the exemplary embodiments of FIGS. 1-3, varying access to worksheets 124, external documents and images 126, provider data 128, exam worksheets 204, reports 206, and modules 208 can be displayed and accessed, based upon the login type detected by log in screen 110.

An exemplary interface 1300 for log in screen 110 is described in detail below with reference to FIG. 13. According to embodiments of the invention, modules 208 include plurality of modules 208 configured to perform specific functionality for personal health information systems 100-300. For example, log in screen may invoke a registration module 208 and when a patient accesses a web interface by directing an Internet browser to the web site depicted in FIGS. 13 and 14, a user can attempt to log into the site using log in screen 110. In an embodiment, if the user is a first time user, he or she is directed to register as new user. In this embodiment, a screen activated choice directs patient 112 to a registration process screen, which invokes a registration process. An exemplary registration process screen is described below with reference to FIG. 14. According to an embodiment, such registration process occurs with standard security for information transfer (for example HIPAA-compliant 32 or 64 bit encryption may be used). In an embodiment, registration requires standard demographic data input and development of a secure (i.e., 'strong') password. In an embodiment, the registration process also requires development of unique user name and a functional e-mail account. The registration process may then send password and account information to the new user's e-mail for confirmation in order to activate the patient's account. A lost or forgotten password or user name may be retrieved by the registration module 208 provided appropriate responses to pre-defined security questions are received. An administrative process creates a unique identifier for user, the unique user ID 120 of FIG. 1. This administrative process may also tag demographic information and further data input by patient 112 or other uses, to user, through unique user ID 120. The administrative process may then confirm that patient 112 is a registered user.

In accordance with an embodiment, exam worksheets 204 may be constructed based on a series of questions wherein some of the questions have a drop down box in a graphical user interface (GUI) which provides a choice of answers. For example, a drop down 'symptoms' menu can include a plurality of chief complaints for a patient 112. Such complaint choices can include, but are not limited to, dandruff, itchy eyes, runny nose, sore throat, headache, stiff neck. After selection of a chief complaint, a relevant, context-sensitive follow-up drop down menu is displayed to select how long the complaint (i.e., symptom) has existed. For example, if a patient 112 complains of a sore throat, a drop down menu to select 'less than three days of symptoms' or 'more than three days of symptoms.' Other data values from a medical exam can be selected and/or entered in exam worksheet 204. For example, values for observations made during medical exams (i.e., 'fever less than 102 F' or 'fever greater than 102 F') can be selected. Depending on the reported complaints/symptoms, other observation values such as, but not limited to 'pharynx injected, no exudates' 'pharynx injected, exudates present', adenopathy absent/present', meningismus absent/present', and 'CSF cultures positive/negative' can be selected. The values entered in an exam worksheet 204 can be used by a healthcare provider 114 to aid in making a diagnosis. For example, to diagnose a viral syndrome, a complaint of a runny nose or sore throat for less than three days accompanied by a fever of less than 102 F may be followed by inspecting the patient's 112 pharynx and observing no exudates. Alternatively, a diagnosis of strep throat may be made after receiving a complaint of a sore throat for more than three days accompanied by a fever of more than 102 F may be followed by inspecting the patient's 112 pharynx and observing exudates.

An exemplary GUI for exam worksheets 204 is provided in FIGS. 18-29, which are described below. In one embodiment, each worksheet question provides a text box for free-text entry in cases where an answer does not appear in a drop down box. When appropriate, after an exam question is answered, option box is activated. In an embodiment, an option dialog box can prompt the provider to determine if there is another answer to the same question. If so, a question may be re-presented in the GUI. In an embodiment, this process repeats until an answer to an option box query is no. For example, an allergy worksheet may present a series of questions pertaining to allergic reactions or symptoms until a 'no' response is received. Once answer is no, the provider can proceed to the next question in a given worksheet. This is depicted in FIGS. 18-29. In embodiments, some questions can cause an expanded field to open. For example, if a question is "Is there an attorney associated with this case?" and the answer is yes, then an expanded field is opened to request pertinent contact information regarding the attorney in question. Such an expanded field may be part of an accident worksheet. Once the worksheet is completed by a registered patient or a healthcare provider, all entries can be reviewed, and entries can be changed or edited. Once a registered patient or provider has completed, reviewed and edited data to their satisfaction, the worksheet can be saved. Worksheets 204 can be viewed by providers and registered patients at a later date. Entries can be changed or edited at later date. A registered patient has the option to allow other registered users, specifically but not only registered providers, to view the data on their worksheets. A registered patient can grant this access for a time specific or in a time-limited manner, as discussed above with reference to FIG. 1.

FIG. 2 illustrates how providers 114 access, edit, and review worksheet information and convert it into medical records 232, in accordance with an embodiment of the present invention. FIG. 2 is described with continued reference to the embodiments illustrated in FIG. 1. However, FIG. 2 is not limited to those embodiments.

As shown in FIG. 2, upon detecting a login by a provider 114 with unique user ID 120, access 122 is provided to worksheets 124 and other medical data. In an embodiment, access 122 is via a module configured to provide access to a HIPAA-compliant secure web site 118, which enables access to the worksheet data. In embodiments of the invention provider 114 may be one or more of a personal health record (PHR) vendor, a healthcare provider, a pharmacy, a hospital, a medical clinic, an assisted living facility, a government organization, or an insurance company. A healthcare provider may be, but is not limited to a physician (i.e., a medical doctor/MD), a nurse practitioner, a surgeon, a psychiatrist, a physical therapist, and a mental health counselor.

As shown in FIG. 2, upon detecting a login by an administrator 116, the administrator 116 is granted control 202 over access to patient and business data. For example, an authenticated administrator 116 can grant, remove, and modify access privileges 230 to worksheets 124, external documents/images 126, exam worksheets 204, reports 206, and modules 208.

In the exemplary embodiment of FIG. 2, access 122 is granted to providers 114 and administrators 116 to a plurality of worksheets 124, external documents/images 126, exam worksheets 204, reports 206, and modules 208. As shown in FIG. 2, based upon access privileges 230, an administrator 116 or provider 114 may enter, review, and annotate data in worksheets 124. In an embodiment, this worksheet data can be converted into a medical record 232. According to an embodiment, this conversion is performed by a conversion routine or module 208 comprising instructions to convert at least a portion of the worksheet data into a medical record 232. Such conversion of worksheet data fields and elements into a medical record 232 may be achieved by mapping, via conversion routine or module 208, a plurality of data fields selected, entered, and updated in worksheets to data fields of a medical record 232. A non-limiting example of an interface for data entry and update of such worksheet data fields is depicted in FIGS. 18-29.

With continued reference to FIG. 2, providers 114 are granted access 122 to exam worksheets 204. In an embodiment, access privileges 230 for providers 114 comprise privileges to enter, review, annotate, and convert exam worksheet 204 data into medical records 232. Providers 114 and administrators 116 can also be granted access 122 reports 206. In embodiments, reports 206 comprise one or more of billing, clinical, spectral array, and SOS reports. Spectral arrays are described below with reference to FIGS. 5 and 7-9, SOS reports are described below with reference to FIG. 6. As shown in FIG. 2, providers 114 and administrators 116 can also be granted access 122 to routines or modules 208. In embodiments, modules 208 comprise one or more of a worksheet module, a view reports from exam module, a scheduling module, a file management module, an insurance module, a demographic module, a pharmacy schedule, and other downstream provider scheduling modules. Example embodiments of the scheduling, pharmacy and file management modules 208 are described below with reference to FIG. 3.

FIG. 3 further illustrates how administrators 116 access and control access to medical information, in accordance with an embodiment of the present invention. FIG. 3 is described with continued reference to the embodiments illustrated in FIGS. 1 and 2. However, FIG. 3 is not limited to those embodiments.

As shown in FIG. 3, an administrator 116 grants control 202 over access 122 to worksheets 124, exam worksheets 204, reports 206 and modules 208. Administrator 116 also has administrative controls 302. In the embodiment of FIG. 3, administrative controls 302 comprise controls over medical data content/form and access to the data in addition to controlling participation by pharmacies and other downstream providers. As illustrated in FIG. 3, an administrator 116 may be an administrator 330 responsible for servicing medical records 232. According to an embodiment, administrator 116 may also have privileges to control a system 304 configured to implement the embodiments described above with reference to FIGS. 1 and 2. For example, administrator 116 may control system 304 by creating, editing, and/or deleting unique user IDs 120 for patients 112, providers 114 and other administrators 116.

Example embodiments of the scheduling, pharmacy and file management modules 208 are described in the following paragraphs.

Scheduling Module

With continued reference to FIGS. 2 and 3, a scheduling module 208 is configured to generate schedules in addition to work orders and referrals for downstream services to be performed by downstream providers. In an embodiment, scheduling module 208 performs automated scheduling according to preferences (ASAP). A scheduling module 208 can be invoked to receive input from a registered patient 112. Such received input may include entry of specific preferences for services that may be requested by providers 114. In embodiments, these preferences may be one or more of insurance plan participation, location, hours of operation, quality measures, parking availability and other amenities. When a specific service is requested by a provider 114, sites providing the requested service can be listed by scheduling module 208. Specific, provided preferences can then filter these sites by preference priority. At this point, a registered patient 112 can view, in a display presented by scheduling module 208, available time slots at these sites to schedule the requested service. According to an embodiment, an administrator 116 is responsible for registering these sites into scheduling module 208 (i.e., administrative responsibilities 332 include registration of these sites). Administrative responsibilities 332 may include indicating specifics of one or more of the above-listed preferences. Administrative responsibilities 332 may further comprise maintaining the schedule from these sites and for the secure transfer of pertinent demographic, insurance, clinical and service request data from the requesting healthcare provider 114 to the service provider. In this way, this transfer of data eliminates the need to duplicate the process of obtaining this same data at the next site of service. This process also removes the requesting healthcare provider 114 from the process of determining which site is chosen by the patient 112 for a requested service. This process also reduces the workload of staff of the requesting and providing sites in the obtainment, transmission of and probable duplication of data. In an embodiment, this process may generate revenue by administrator 116 by charging a fee for service provider registration and screen space in an interactive interface presented by scheduling module 208. In this way, the ASAP scheduling performed by scheduling module 208 improves both the efficiency and revenue potential of scheduling downstream services.

Pharmacy and Prescription Modules

As shown in FIGS. 2 and 3, a pharmacy module 208 may be configured to generate prescriptions. Downstream providers may be, but are not limited to, pharmacies. The pharmacy module 208 can be used to perform a similar process as described above with reference to scheduling module 208, but is specific to pharmacies and prescriptions. For example, instead of scheduling a time slot for a service, the requesting healthcare provider 114 submits a prescription electronically. By invoking pharmacy module 208, a registered patient 112 can specify their pharmacy preferences. These preferences may include, but are not limited to, pharmacy location, pharmacy hours, price specifics for specific products, and availability of generic drugs as opposed to brand (trade) name drugs. Preferences can also include participation in a patient's 112 pharmacy benefits program. At this point, a requested prescription is transmitted to the pharmacy that meets the patient's 112 indicated preferences. In an embodiment, an administrator 116 has administrative responsibilities 332 for maintaining pharmacy information used by pharmacy module 208 and for the secure transfer of pertinent demographic, insurance, clinical and service request data from the requesting healthcare provider 114 to a given pharmacy. As noted above with reference to scheduling module 208, this transfer of data eliminates the need to duplicate the process of obtaining this same data at the pharmacy while also removing the requesting healthcare provider 114 from the process of determining which pharmacy is chosen by the patient for filing a requested prescription. In an embodiment, each medication contributes to the spectral array, in that body system specific medications, for example, cardiac medications, "contribute" to the cardiac body system "display". One feature of the healthcare provider's 114 prescription module 208 is that each medication listed in the formulary is "tagged" to a single or multiple body system.

According to an embodiment, a prescription module 208 is configured to operate in conjunction with pharmacy module 208 described in the preceding paragraph. By making selections in an interactive interface presented by pharmacy module 208, a healthcare provider 114 can choose specific medications, dosages, frequency, route of administration (i.e., oral/liquid suspension, oral/pill, syringe, patch, topical, et al.), number dispensed, refill number(s) and instructions. According to an embodiment, an administrator 116 has administrative responsibilities 332 for tracking prescriptions for each registered patient 112 by healthcare provider 114.

Exam Modules

In an embodiment, a plurality of exam modules 208 (not shown) are configured to process data from one or more exam worksheets 204. Exams can be categorized as a general exam or specialty exams. According to embodiments of the invention, each examined body part has corresponding responses or answers, which are either populated in drop down boxes or entered as free text in exam worksheets 204. In this way, some exam answers can be standardized. In an embodiment of the present invention, exams are compliant with Health Care Financing Administration (HCFA) and Centers for Medicare and Medicaid Services (CMS) requirements for completeness.

According to an embodiment, an administrator 116 can generate a plurality of reports 206 based upon data compiled by exam modules 208. For example, exam modules 208 can generate a tally report 206 for items examined. When compiled in a tally report 206, items examined and questions answered in an exam worksheet 204 can generate a billing report 206 that accurately reflects the level of service provided. Based upon the level of service provided, the correct charge for services for each encounter can be determined. In one embodiment, a level of service can be a numeric range (i.e., 1-5).

An administrator 116 can also tally a clinical report 206 compiling pertinent answers and exam findings. Administrators 116 and healthcare providers 114 can utilize history and exam findings in a spectral array report 206 with weighting. For example, a clinically relevant format for scoring or weighing medical data based on a scale of increasing objectivity may weigh data elements as indicated in Table 1 below.

TABLE 1

Example Weighting for Data Elements

| Source of Medical Data Element | Weight |
| --- | --- |
| Subjective complaint (i.e., a 'chief complaint from a patient) | 1 |
| Historical Information | 2 |
| Physical Exam Finding | 3 |
| Ancillary Data Finding (i.e., serologic, radiologic, or physiologic) | 4 |
| Intervention (i.e., medication or therapy) | 5 |
| Procedure | 6 |
| Surgery | 7 |

In another embodiment, data elements (i.e., responses to worksheet questions) reported by patients 112 (i.e., 'chief complaints') have a weighting value of 1, medical history data elements have a weight of 2, exam data elements have a weight of 3, data elements related to diagnostic tests have a weight of 4, and data elements associated with medical procedures performed on the patient 112 have a weight of 5. The increasing weights for the above-listed data elements are assigned based on the increasing levels of reliability for complaints reported by a patient 112 as compared to data from a medical history, exam, diagnostic, and procedure for the patient 112 have increasing levels of reliability and significance. For example, a runny nose may come and go, but a rhinoplasty with a poor outcome (i.e., a botched nose job) has a greater impact and is therefore more significant. After being weighted, data elements are mapped to a Spectral array reports 206 are described below with reference to FIGS. 5 and 7-9.

Ancillary Data Review Module

In an embodiment, a healthcare provider 114 can invoke an ancillary data review module 208 to view reports 206 as well as external documents and images 126 tagged to a registered patient 112 data file. An ancillary data review module 208 is configured to enable a healthcare provider 114 to annotate these items. For example, ancillary data review module 208 allows a provider 114 to note these items as having been reviewed. Additionally, an administrator 116 can utilize the time spent by a provider 114 or complexity of data reviewed to generate a corresponding billing report. Examples of ancillary data may include, but are not limited to, serologic data from a blood test, radiological data from an X-ray or scan, and physiological data from an electrocardiograph (EKG/ECG) or electroencephalography (EEG).

Reports 206 can also be compiled by other modules 208 such as, but not limited to history modules, diagnosis modules, and treatment and plan modules. For example, if provider 114 performs a history by recording answers from a history worksheet and or reviews data from a worksheet and indicates the review with a date/time stamp and signature, for government and third party billing purposes these are equivalent activities, and this is work is considered to be done and billable. The billing codes may be exam and management (E&M) codes including history, diagnosis and treatment plan activities.

Worksheet Workflow

FIG. 4 shows an exemplary embodiment of a worksheet workflow 400 of the present invention comprising a data grid 410. FIG. 4 is described with continued reference to the embodiments illustrated in FIGS. 1-3. However, FIG. 4 is not limited to those embodiments.

Worksheet workflow 400 begins when a user, such as a patient 112 or provider 114, enters data into a worksheet 124. In embodiment, the data entered into worksheet 124 can be securely stored and subsequently transmitted (i.e., after encryption). Worksheet data can be viewed by providers 114 and edited, corrected, annotated and then "converted" to a medical record 232. The resulting medical record 232 can be stored and transmitted.

A plurality of worksheets 124 are available to patient users. Such worksheets 124 include, but are not limited to a chief complaint worksheet, a history of present illness worksheet, an accident worksheet, a collision worksheet, an allergy worksheet, a medication worksheet, a past medical history worksheet, a surgery worksheet, a family history worksheet, a social history worksheet and a review of systems worksheet. These worksheets 124 are also available to providers 114.

As shown in FIG. 4, data grid 410 comprise data culled from 10 worksheets 124, wherein each worksheet 124 comprises 10 questions. In this example, data grid 410 is the 10×10×10 data grid 410 depicted in FIG. 4. Each cell or 'pixel' within data grid 410 represents a data point, wherein each data point can be 'tagged' based on several criteria.

In the example embodiment provided in FIG. 4, the criteria may include, but are not limited to reviewed/examined, not reviewed/examined, normal, abnormal, and body system criteria. For example, the reviewed and/or examined criteria provides a tally report 206 indicating a cumulative level of service and appropriate billing level. As shown in FIG. 4, the service and/or billing levels may correspond to codes indicating levels (i.e., levels 1-5). The normal and abnormal criteria may be used to provide a summary report 206. As shown in FIG. 4, the abnormal criteria may constitute a "clinical report" 206. Such a clinical report 206 allows for grid-to-grid comparison and correlation for SOS. A diagnosis can be based on both exam elements and history elements as well as ancillary data elements. According to embodiments, a billing report or tally report 206 will include an billable work, from filling out or reviewing history worksheets, exam worksheets and ancillary data worksheets in addition to diagnosis, treatment and plan worksheets. Similarly, clinical reports 208 can include pertinent data from all these sources. In an embodiment, the SOS report will do the same, as will the spectral array report. Use of the spectral array report will allow providers 114 to readily identify patients with complaints in most or all body systems, but who has no exam findings. The provider 114 can then utilize the history module data even if they do not provide the original data entry used to enter the historical data. In this way, embodiments of the invention leverage data provided by others, such as patients 112, by allowing providers 114 to easily analyze it via SOS reports and spectral arrays. The use of data grid 410 for an SOS is described below with reference to FIG. 6. The body system criteria can be used to generate a summary report 206 of "abnormals", segregated by body system. Such summary reports 206 enable generation of Spectral Array reports 206. Spectral arrays are described below with reference to FIGS. 5 and 7-9.

FIG. 5 illustrates a mapping 500 of worksheet elements, such as data types 505 to body systems, in order to create spectral arrays. In accordance with an embodiment of the present invention, mapping of data types 505 to one of eight body systems is used to create spectral arrays 510 and 520 depicted in FIG. 5. FIG. 5 is described with continued reference to the embodiments illustrated in FIGS. 1-3. However, FIG. 5 is not limited to those embodiments. For example the US government has specified 14 body systems, whereas the exemplary embodiment of FIG. 5 depicts only eight.

As shown in FIG. 5, data types 505 can include, but are not limited to a patient subjective complaint, a history element, an exam element, an ancillary data element, a procedure element, and a surgery element. An exam element can be a data item (i.e., a received response or a data field value representing an answer to a worksheet question) from an exam worksheet 204. Similarly, a patient subjective complaint can be a data item received from a patient 112. For example, patient subjective complaints can be received as a response to a question in a worksheet 124. An ancillary data element can be a data item representing data received by ancillary data review module 208 described above.

In an embodiment, a spectral array module 208 is configured to weigh a plurality of data elements corresponding to various body systems, wherein each of the data elements have a data type (such as, but not limited to data types 505 provided in FIG. 5).

In the example spectral arrays 510 and 520 provided in FIG. 5, there are eight body systems represented. Spectral arrays 510 and 520 enable the reduction of complex medical histories to body system coded displays with color, symbols and timelines graphically depicting the 'whole story' of a patient's medical history.

The scale of a spectral array is one of increasing objectivity and level of intervention. In addition to body system specific color-coding for pixels comprising icons in spectral arrays, the icons can also be coded based on a level of severity for a symptom or patient complaint. In one embodiment, such severity coding is a numeric range (i.e., 1-6). In an embodiment, each line of icons (comprising color-coded pixels) in spectral arrays 510 and 520 represent a timeline of contiguous encounters with a given patient 112.

Spectral array 510 is an exemplary spectral array for a patient with a history (i.e., historical data), exam, and ancillary data supportive of a reported complaint who has received timely interventions addressing symptoms related to the complaint. As illustrated in FIG. 5, spectral array 510 indicates a convergence of icons representing historical, exam, and ancillary data within one of the eight body systems shown in the spectral array.

Spectral array 520 is an example spectral array for patient with many self-reported complaints, but without "objective" data. This is why the icons of spectral array 520 do not 'converge' into any single body system and are instead dispersed across the eight body systems.

Figure 6:
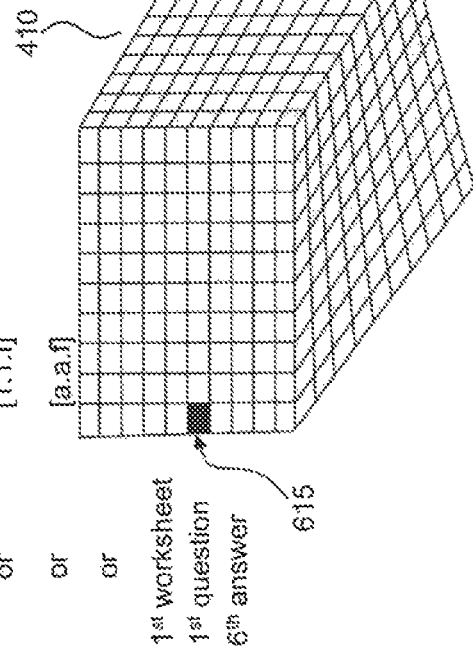
FIG. 6 depicts how worksheet responses are translated into a grid for diagnosis, in accordance with an embodiment of the present invention.

FIG. 6 depicts a translation 600 of diagnosis worksheet responses into a grid for diagnosis and an SOS report, in accordance with an embodiment of the present invention. FIG. 6 is described with continued reference to the embodiments illustrated in FIGS. 1-4. However, FIG. 6 is not limited to those embodiments.

As shown in FIG. 6, a grid 410 can be correlated or logically connected to a diagnosis worksheet 124. A healthcare provider 114 can assign a diagnosis and associated ICD-9 or ICD-10 code to a registered patient 112 for a particular encounter (i.e., office visit or exam) based on data from one or more worksheets 124, exams, exam worksheets 204 and from ancillary data (i.e., data received by ancillary data review module 208 discussed above). An administrator 116 can use data field analysis to compare a field associated with a diagnosis to another field associated with the same diagnosis. The degree of correlation provides substantiation (i.e., a standard of substantiation) of the diagnosis in second and subsequent uses. In one embodiment, this correlation may be a percent figure. Acceptable percentages or ranges of percentages can be determined by administrator 116 for provider 114-to-self correlation. Acceptable percentages can also be determined by the administrator 116 for provider-to-group correlation. Additionally, acceptable percentages can be determined by the administrator 116 for provider-to-network correlation. Acceptable percentages can also be determined by administrator 116 for provider-to-region correlation. Such correlations result in the generation of a standard of substantiation (SOS) report 600 provided in FIG. 6.

As shown in FIG. 6, grid 410 is connected to a diagnosis. In the example embodiment of FIG. 6, grid 410 can be represented as a digital code. For a given worksheet 124, ("Worksheet 1" in the example of FIG. 6), when a response is received (i.e., "Answer 6") for a question (i.e., "Question 1"), the response can be represented as the digital code of [1.1.0000010000], wherein "1.1" represents Worksheet 1 and Question 1 and the numeric string "0000010000" represents Answer 6, out of 10 possible answers. In embodiments of the invention, worksheets 124 and exam worksheets 204 comprise a plurality of questions, which in turn each have one or more possible answers or responses. The possible answers may be populated in a database lookup table used to display drop down menus or dialog boxes presented to a user so that the user a provider 114) can select the appropriate response. In the example embodiment of FIG. 6, the 10 possible answers for question 1 in worksheet 1 may be presented as a list in a drop down menu in an interactive interface, and in response to determining that a user has selected the sixth of answer, the answer is encoded as "0000010000".

In an alternative embodiment, the selection of answers for worksheet questions can be represented as alphanumeric strings. For example, the $6^{th}$ response to question 1 in worksheet 1 can be represented as "[1.1.f]" wherein "1.1" represents Worksheet 1 and Question 1 as discussed above and the letter "f" represents Answer 6 (f being the $6^{th}$ letter of the alphabet). In another embodiment, the $6^{th}$ response to question 1 in worksheet 1 can be represented as "[a.a.f]" wherein the string "a.a" represents Worksheet 1 and Question 1 (a being the $1^{st}$ letter of the alphabet) and the letter "f" represents Answer 6 (f being the $6^{th}$ letter of the alphabet). These embodiments may reduce data storage requirements and/or simplify processing of worksheet responses in cases where there are less than 26 possible responses. An advantage of converting responses to worksheet 124 and exam worksheet 204 questions is that it quicker more accurate for providers 114 and administrators 116 to review the digital format for correlations. Embodiments of the invention improve the accuracy of diagnoses by employing standards of substantiation (SOS). By generating SOS reports, a determination an be made as to whether a third party will approve a payment or service. In this way, embodiments of the present invention achieve efficiency improvements over current techniques by reducing the number of employees needed to perform this task. This is because currently available techniques and systems require human manual review of analog records to perform this task, while embodiments of the invention enable allow automated, non-human review to perform the same task through the use of digitized data.

FIG. 7 illustrates an exemplary embodiment of how worksheet data is used for spectral array analysis 700. In particular, FIG. 7 shows how spectral arrays are used to identify relevant patient education directed links (PEDLs). The value of spectral arrays, such as spectral arrays 710 and 720, is that they enable display of PEDLs that are relevant to a patient 112 based on their body system specific ailments and complaints.

As shown in FIG. 7, one advantage of generating spectral arrays 710 and 720 is that they enable PEDLs to be presented to a patient 112, wherein the relevance of the PEDLs is driven by icons presented in various body systems of the spectral arrays. However, as noted in FIG. 7, no personal health information (PHI), personal identifying information, or demographic identifiers are displayed in spectral arrays 710 or 720.

In an embodiment, PEDLs comprise directed educational links (i.e., hyperlinks or Universal Resource Locators/URLs) that have been determined to be relevant to a registered patient 112. The relevance of the education links are based at least upon the patient's body system specific ailments and reported complaints, as well as medical history data, physical exam finding and ancillary data, procedure and surgical history, as displayed in spectral arrays 710 and 720.

In spectral array 710, icons are displayed in body systems 2 and 4 for an example patient, patient. A. Based on the number of icons and severity level (i.e., color coding of the icons) displayed in body system 2 of spectral array 710, there is significant "interest" in diseases/products/information affecting body system "2." Similarly, based on the icons displayed in body system 4, there is some "interest" in diseases/products/information affecting body system "4," According to an embodiment, PEDLs with information on diseases and products, such as, but not limited to therapies, services, prescription drugs, over the counter drugs, and medical devices, related to body systems 2 and 4 will be presented to patient A. For example, links/URLs with information related to body systems 2 and 4 can be presented in an interactive interface so that patient A may select, using an input device, one or more of the presented links.

In spectral array 720, several icons are displayed in body system 7 for another example patient, patient B. Based on the convergence of icons in body system seven of spectral array 720, there is significant "interest" in diseases/products/information/services affecting body system 7. In accordance with an embodiment of the invention, PEDLs with information related to body system 7 are presented in an interactive interface so that patient B may select, using an input device, one or more of the presented links.

Figure 8:
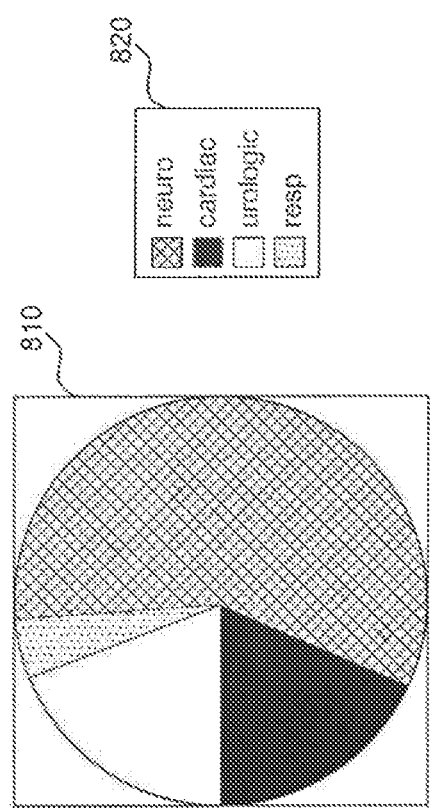
FIGS. 8 and 9 illustrate an embodiment of the invention utilizing graphical displays mapping worksheet responses to body systems.
Figure 9:
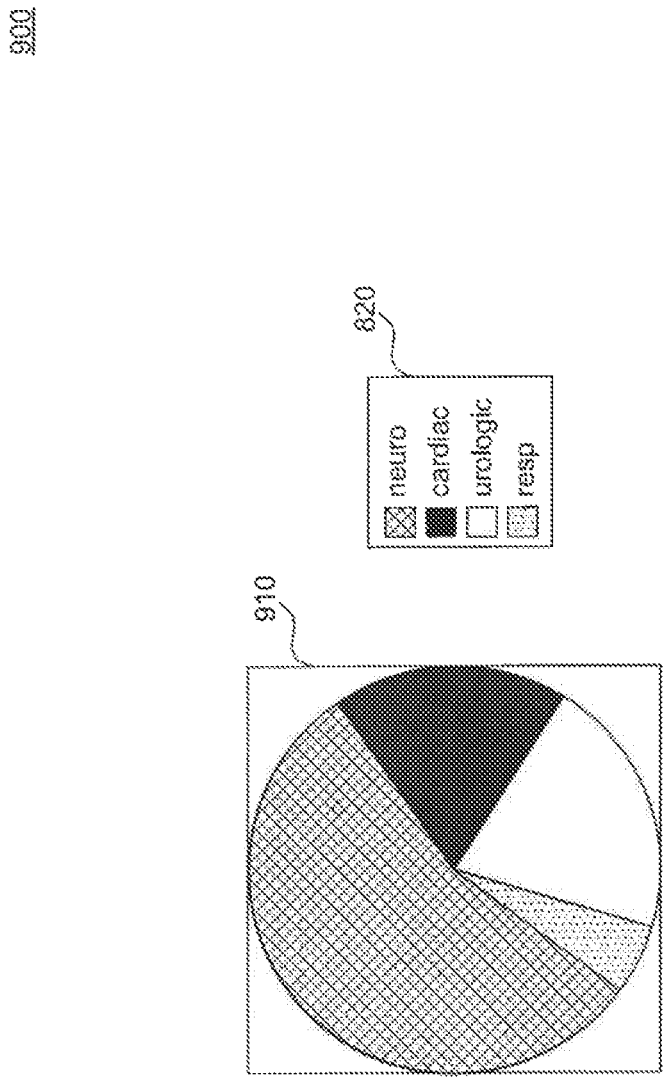

FIGS. 8 and 9 illustrate an embodiment of the invention utilizing graphical displays mapping worksheet responses to body systems to perform spectral analysis. In particular spectral arrays 810 and 910 of FIGS. 8 and 9, respectively, enable spectral analysis of body systems of a patient whereby 'at a glance' analysis of a patient's 112 present state of health and past medical history can be quickly accomplished.

FIG. 8 illustrates a mapping 800 of worksheet responses to body systems 820. As shown in FIG. 8, display 810 maps worksheet responses mapping to body systems 820. In the exemplary embodiment of FIG. 8, body systems 820 include neurological, cardiac, urologic, and respiratory systems. It will be understood by those skilled in the relevant art(s) that body systems 820 can include additional body systems not shown in FIG. 8, such as, but not limited to, gynecological, vascular, endocrine, pulmonary, allergy, gastrointestinal (GI), ear/nose/throat (ENT), and psychiatric body systems (see FIG. 11).

In the example of FIG. 8, a patient 112 has had 20 total neurological data elements. In this example embodiment, data elements are weighted based upon their relative reliability, relevance, and importance. For example, responses to worksheet questions reported by patients 112 as 'chief complaints' may have a weight of 1 and more reliable or important data elements such as medical history data elements have a weight of 2. Further, for example, medical exam data elements (i.e., responses to exam worksheet 204 questions) may have a weight of 3, data elements related to diagnostic tests may have a weight of 4, and data elements associated with medical procedures performed on the patient 112 may have a weight of 5.

With continued reference to FIG. 8 and using the exemplary weights indicated above, the medical history of a patient 112 with the data elements listed in Table 2 below may be depicted as shown in spectral array 810. In this example, the patient has complained of lower back pain, right leg pain, and numbness and who has a significant history of chronic cough has been examined. The examination reveals that the patient has a tender spine, limited straight leg raising, and decreased sensation. X-rays of the patient reveal degenerative disc disease and a MRI reveals a disc herniation. The patient in this example has a medical history including a myocardial infarction, a triple heart by-pass, prostate cancer and a transurethral resection of the prostate (TURP) procedure. This patient's medical history is summarized in Table 2 below. In an embodiment, the patient's medical history elements are mapped to body systems or 'spectral categories' and weighted as shown in Table 2. The total and weighted values can then be graphically depicted in spectral arrays 810 and 910, as shown in FIGS. 8 and 9, respectively.

FIG. 9 illustrates another mapping 900 of worksheet responses to body systems 820. Spectral array 910 of FIG. 9 shows similar results based on the weighted values from Table 2. Based on the 'snapshots' provided by spectral arrays 810 and 910, a healthcare provider 114 can quickly and accurately assess the patient's current health status and determine that the patient has significant neurological medical history. In an alternative embodiment, the simple weighting system discussed above and shown in Table 2 can be modified. For example, a higher weight can be assigned to some history elements to indicate that a triple by-pass cardiac procedure is more significant than a transurethral resection of the prostate (TURP) urological procedure to treat prostate cancer. In other embodiments, each body system of a spectral array is assigned a separate color.

FIG. 10 depicts sign in authorization levels (SINAL) and their associated privileges, in accordance with an embodiment of the present invention. FIG. 10 is described with continued reference to the embodiments illustrated in FIGS. 1-3 and 7. However, FIG. 10 is not limited to those embodiments. In particular, FIG. 10 provides a detailed breakdown of the access privileges 230 and privileges needed to perform administrator responsibilities 332 described above with reference to FIGS. 2 and 3.

As shown in FIG. 10, upon detecting a secure log in by a registered patient 112, healthcare provider 114, or administrator 116, base privileges 1010 are granted to the logged in user, in the example embodiment of FIG. 10, base privileges 1010 enables access to a web site including data entry screens for worksheets 124 by either a patient 112 or provider 114. Base privileges 1010 also enable the logged in user to securely store entered data via a HIPAA-compliant mechanism. For example, data entered in worksheets 124 may be encrypted for subsequent transmission and storage in a secure database or data store. Base privileges 1010 also enable the logged in patient 112 to grant access to data to a healthcare provider 114 or for a healthcare provider 114 to grant access to another healthcare provider (including a downstream provider).

With continued reference to FIG. 10, upon detecting a secure login by a healthcare provider 114, provider privi-

TABLE 2

Patient Medical History

| Body System | Complaints (weight = 1) | History (weight = 2) | Exam (weight = 3) | Diagnostic (weight = 4) | Procedure (weight = 5) | Total (wgt) |
|---|---|---|---|---|---|---|
| Neurologic | 3 | 9 | 8 | 0 | 0 | 20 (45) |
| Cardiac | 0 | 2 | 0 | 0 | 5 | 7 (29) |
| Urologic | 0 | 2 | 0 | 0 | 5 | 4 (29) |
| Respiratory | 0 | 2 | 0 | 0 | 0 | 2 (4) |

As shown in Table 2 and in spectral array 810, a patient 112 reporting neurological 'chief complaints', having 9 medical history data elements, and 8 exam data elements will have a spectral array indicating a relatively large amount of neurological medical history as compared to other body systems or 'spectral categories,' Spectral array 810 also displays the relatively larger amount of worksheet 124 and exam worksheet 204 responses related to the cardiac and urologic body systems 820 as compared to the respiratory body system.

leges 1020, including all of the aforementioned base privileges 1010, are granted to the provider. As shown in FIG. 10, provider privileges additionally include worksheet review, annotation and correction, and submission of a worksheet 124 as a medical record 232. Provider privileges 1020 also allow provider 114 to record and securely store documentation and external documents and images 126 as part of a medical record 232 for a patient 112. Lastly, provider privileges 1020 grant a logged in provider 114 the ability to grant access to a medical record 2343 to downstream providers and third party entities.

FIG. 10 also illustrates administrator privileges 1030 and super administrator privileges 1040 granted to administrators 116. As shown in FIG. 10, upon detecting a secure log in as an administrator 116, administrator privileges 1030 are granted, which include permissions for the logged in administrator 116 to edit, modify and format worksheets 124, exam worksheets 204, medical records 232, and reports 206. Administrator privileges 1040 further include permissions to perform data entry via worksheets 124 and exam worksheets 204. Administrator privileges 1040 also enable administrators to determine access to data, medical records 232 and reports 206 to providers 114. Lastly, administrator privileges 1040 also enable administrators 116 to grant data access to third party entities.

With continued reference to FIG. 10, super administrator privileges 1040 may be granted to a set of administrators 116 to contract for customization services related to the system depicted in FIGS. 1-3. Super administrator privileges 1040 also include permissions to contract for scheduling services. As shown in FIG. 10, Super administrator privileges 1040 further include permissions to perform data entry via worksheets 124 and exam worksheets 204. Super administrator privileges 1040 include permissions for a logged in 'super administrator' to contract for diagnosis substantiation services. As noted above with reference to FIG. 6, the invention achieves increased efficiency as compared to current techniques because less employees are needed to contract for diagnosis substantiation services, thus enhancing revenue stream generation. Lastly, super administrator privileges 1040 include permissions for super administrators to contract for educational and information distribution services. For example, super administrators can contract for educational information included in PEDLs links described above with reference to 7.

Figure 11:
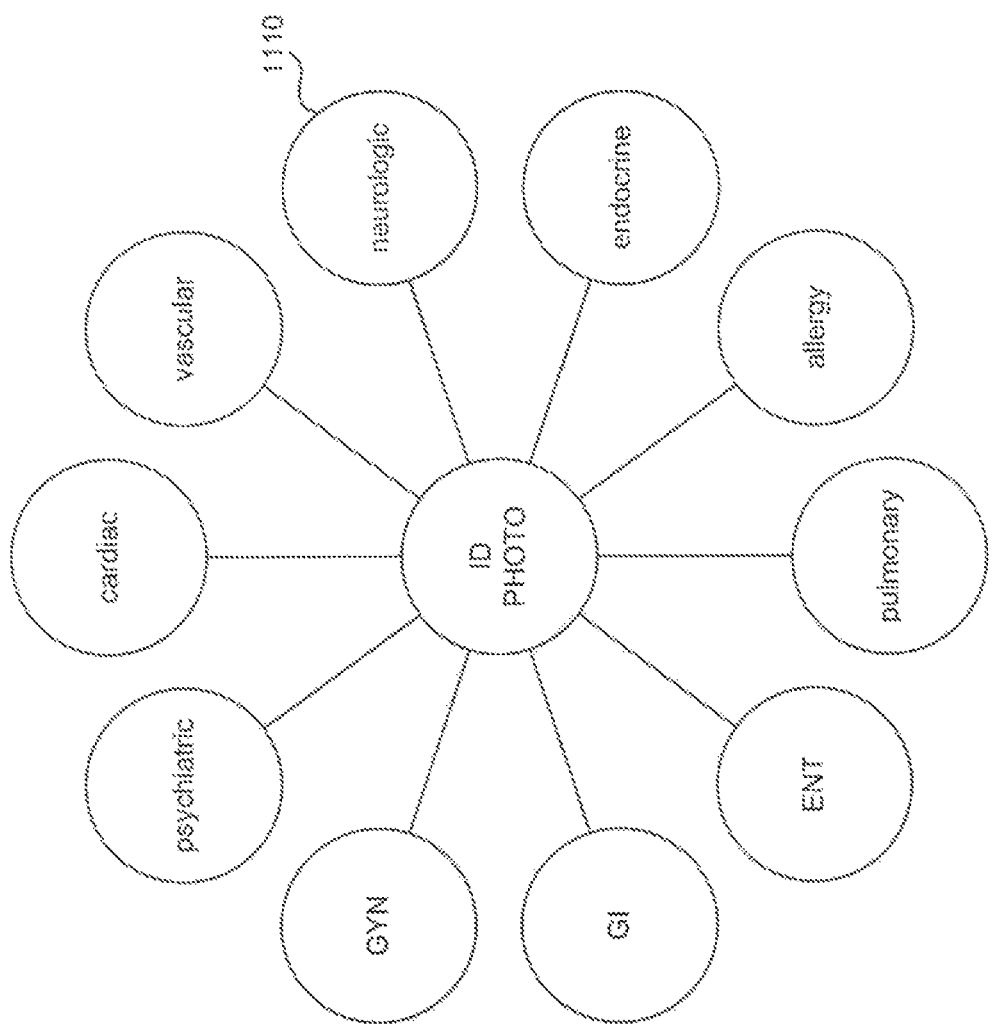
FIG. 11 illustrates the body systems for a patient, in accordance with an embodiment of the present invention.

FIG. 11 illustrates a mapping 1100 of body systems to a patient, in accordance with an embodiment of the present invention. In particular, FIG. 11 depicts a set of body systems 1110 for a registered patient 112.

In the example embodiment of FIG. 11, the registered patient 112 is identified by a unique user ID 120 and/or an identifying photo. For example, a component of a unique user ID 120 for a registered patient 112, may include a photo of that patient. As shown in FIG. 11, body systems 1110 include neurological, cardiac, urologic, respiratory, gynecological, vascular, endocrine, pulmonary, allergy, gastrointestinal (GI), ear/nose/throat (ENT), and psychiatric body systems. It will be understood by those skilled in the relevant art(s) that body systems 1110 can include additional body systems not shown in FIG. 11. For example, exam data along with medical history and personal health information mapped to one or more of body systems 1100 can be used to generate more detailed spectral arrays than those depicted in FIGS. 5 and 7-9.

1) Mobile Device Embodiment

A mobile device embodiment of the system depicted in FIGS. 1-3 and interface illustrated in FIGS. 13-29 is provided below. In the mobile client device embodiment, an apparatus such as a mobile device may have mobile device software installed in local memory of the apparatus. Such mobile device may be any wireless mobile device such as a mobile phone, a personal digital assistant (PDA), a smart phone, a hand held computer, a palmtop computer, an ultra-mobile PC, a device operating according to the MICROSOFT™ Pocket PC specification with the MICROSOFT™ WINDOWS™ CE operating system (OS), a device running the GOOGLE™ Android OS, a device running the Symbian OS, a device running the PALM™ OS, a BLACKBERRY™ device, a TREO™ device, or a device running the Apple IPHONE™. The mobile device software may be downloaded from a remote machine and installed through an installation routine, preinstalled on the device, or installed through a flash card, CD, DVD, removable storage (i.e., removable storage unit 3018 depicted in FIG. 30) or other conventional methods.

Using the Mobile Device Software

When the mobile device software is initially installed, in many embodiments, the mobile device's local, secure database will be empty or populated with default information. According to an embodiment, a server may pre-populate a secure mobile device database with the information from the database of the server. In embodiments, the server and the mobile device may be the computing device 3000 depicted in FIG. 30. Mobile device software may allow a user, such as, but not limited to patient 112, provider 114, or administrator 116, to view a number of screens or dialog boxes. Executing mobile device software causes a mobile client device to run a display routine to display the user's worksheet and medical information on a display of the mobile device. In an embodiment, the display 3030 shown in FIG. 30 is the mobile device display. Mobile client device may also use a decryption routine and a storage routine to display the output of the server. The display routine may display one or more Windows within a GUI (see FIGS. 13-29) on display 3030 which may comprise a plurality of command regions, tabs, data entry fields, buttons and icons to initiate routines which enable the mobile device to receive worksheet and medical information from the server which will be used to populate a database of a mobile client device. Worksheet information includes information for all worksheet types, including exam worksheets. Running the reception routine may cause mobile device software to establish a connection with the server to download new information, or there may be a separate connection routine with connection settings to allow the mobile device to connect with the server. Moreover, initiating the reception routine (and possibly the connection routine) will cause the server to output the personal health information through a server output routine, which outputs worksheet data and medical records from the database of the server. In an embodiment, the output routine securely transmits the personal health information. For example, the output routine may encrypt the medical data prior to transmission to one or more designated entities.

2) Using the Mobile Client Device to Access Personal Health Information

As discussed above, a mobile client device can be used to view medical information by invoking the mobile device software on the mobile client device. A similar installation procedure can be followed to allow a patient 112, provider 114, or administrator 116 to download an installation package on a server or personal computer (PC) so that these types of users can install mobile device software on a computer and use mobile device software to view worksheet data and medical information on a display of a server or PC. In an embodiment, such computers and PCs will interface with a web server to distribute and receive worksheet and medical information. While the web server embodiment will be described in detail with reference to FIGS. 13-29 below, an embodiment using just a server could be constructed. For example, a server in an embodiment that does not use a web server could fulfill both server and web server roles.

In an embodiment, a web server hosts a website containing web pages. See FIGS. 13-29. Each web page may contain one or more windows or webforms. See FIGS.

13-29. A user of the system will interface with web pages using a web browser (not shown). To view or modify a user's medical information, a user enters a web address into the terminal's web browser, which allows a display to receive the web pages through web server's web page transmission routine. The web address is the URL of the web server. The first time a particular mobile client device or PC accesses the web server's web page, the web server may transmit a web program to be downloaded from a server (such as a web server) via a web program download routine. Installation of the web program may be initialized using a web program installation routine. The web program may be an applet, ActiveX control, Internet browser, or other software designed to interface with web server or the web server's web pages. The web program may initiate a terminal reception routine wherein the routine requests user to enter the encryption key and identification information (i.e., a unique user ID 120). The web program may cause a webform to appear on the display of a mobile client device or PC, prompting user to enter a key and identification information. A terminal may transmit the identification information to the web server (using the terminal to a web server transmission routine). In some embodiments, a key may also be sent, but in other configurations a key is retained on a terminal.

Once the identification information is received, a registration routine for associating the user's worksheet and medical information with his or her identification information (including, but not limited to unique user ID 120) may be executed by the web server. To create this association, the web server may send the identification information to a server; (via the web server-to-server transmission routine). The server may then search its database (using its search routine) to determine whether there is worksheet and medical information which is associated with the received identification information (including unique user ID 120).

If the search routine identifies corresponding worksheet and medical information, the server may send worksheet and medical information to the web server, using the server transmission routine. Once the web server has worksheet and medical information, it may generate a web page using a web page generation routine if the web server has the encryption key, or the medical information is unencrypted. The web server may transmit the generated web pages to website via the web server to website transmission routine. If worksheet and medical information is encrypted and the web server does not have the encryption key, the web server may simply transmit the encrypted information to a terminal. The web program running on a terminal may receive the encrypted information, decrypt the information by using the encryption key, and display the information using a terminal display routine. If the user does not have any worksheet and medical information associated with the identification information, the server may transmit a notification (using, a notification transmission routine) to the web server that no worksheet and medical information could be found. Upon receipt of this transmission, the web server may request that the user (such as, but not limited to patient 112, provider 114, or administrator 116) provide account identification, notify the user that the medical information was not recognized, and/or create a new account based on the identification information, in an embodiment, this may trigger an alert to administrator 116 that a possible/potential breach has been attempted.

A terminal that receives the medical information (and the web page in certain embodiments) may store the medical information (and perhaps the web page) in memory. Terminal may use a key to decrypt the information using a terminal decryption routine. Having the decrypted medical information in memory, the web program or browser may display the information using the terminal display routine. Terminal may also store the information using a terminal storage routine. Using the terminal display routine, terminal may show or display the medical information on a screen, projection, or a display.

The web page visible to the user, may be programmed using basic HTML, or using a number of complex languages such as C++, Java, Perl, and may take the form of a program, applet, script, or an ActiveX control. In the embodiment just described, a terminal does not need to send a key to the web server. By maintaining a key on a terminal, security will likely be stronger than an embodiment where a key is sent to the web server along with the identification information.

3) Using a PC to View and Edit Medical Information

A described above, a PC can use either mobile device software or terminal software, or both the mobile and terminal versions, to view medical information on the display screen or monitor of a PC. In an embodiment, a PC may be computing device 3000 depicted in FIG. 30 and the display screen may be display 3030. In one embodiment, a PC may receive personal health information from a server through a web server via a server to web server transmission routine and a web page transmission routine if a PC is receiving the type of personal health information a terminal would ordinarily receive. As discussed above, a terminal and a PC may have the same hardware depicted in FIG. 30 and be connected to the same type of network structure (i.e., via network interface/communications interface 3024 and communications path 3026. However, in embodiments, a terminal refers to a computer in a public or semi-public location such as a library computer, school computer, kiosk, workstation, or Internet cafe computer. A PC could receive information from the server's output routine if a PC is running mobile device software. Some adaptations of mobile device software may need to be effected to make sure mobile device software can run on a PC. The registration routine may be programmed to allow a user to select a computer or laptop during the registration routine. The URL transmission routine would locate the URL of a server (or a generic file server, web server, or ftp server) which would direct the user to the appropriate installation package for his or her PC, mobile client device, or terminal. The user, such as a registered patient 112 or a healthcare provider 114 can download and install the package using the installation routine.

A PC also presents an option to implement another way to transfer, display, edit, annotate, and store the worksheet and medical information (though certain types of mobile devices can implement this feature as well). In this method, a secure connection and a username and password are used to transfer the worksheet and medical information, and the server may associate the username and password with a particular set of worksheet and medical information. The worksheet and medical information may be sent through a secure technology to a PC using technologies such as Secure Sockets Layer (SSL), Transport Layer Security (TLS), digital certificates, or technology adhering to the X.509 standard for a public key infrastructure (PKI) for single sign-on (SSO) and Privilege Management Infrastructure (PMI). When the user registers his or her computer with the server, the server will associate a subset of worksheet and medical information with the user's identification information. When the user requests a medical information update, the PC sends the username and password to the server. The server, which then retrieves the corresponding information, using a selection routine, will then send the worksheet and medical information to a PC. To enhance security, SSL or technologies can be used for communications between a PC and the server. To prevent others from accessing unencrypted personal health information on a PC, a PC may encrypt the information once it is received by the PC, using a HIPAA-compliant encryption routine. Similarly, a server may also store its information in an encrypted format as well.

Method Embodiment

Figure 12:
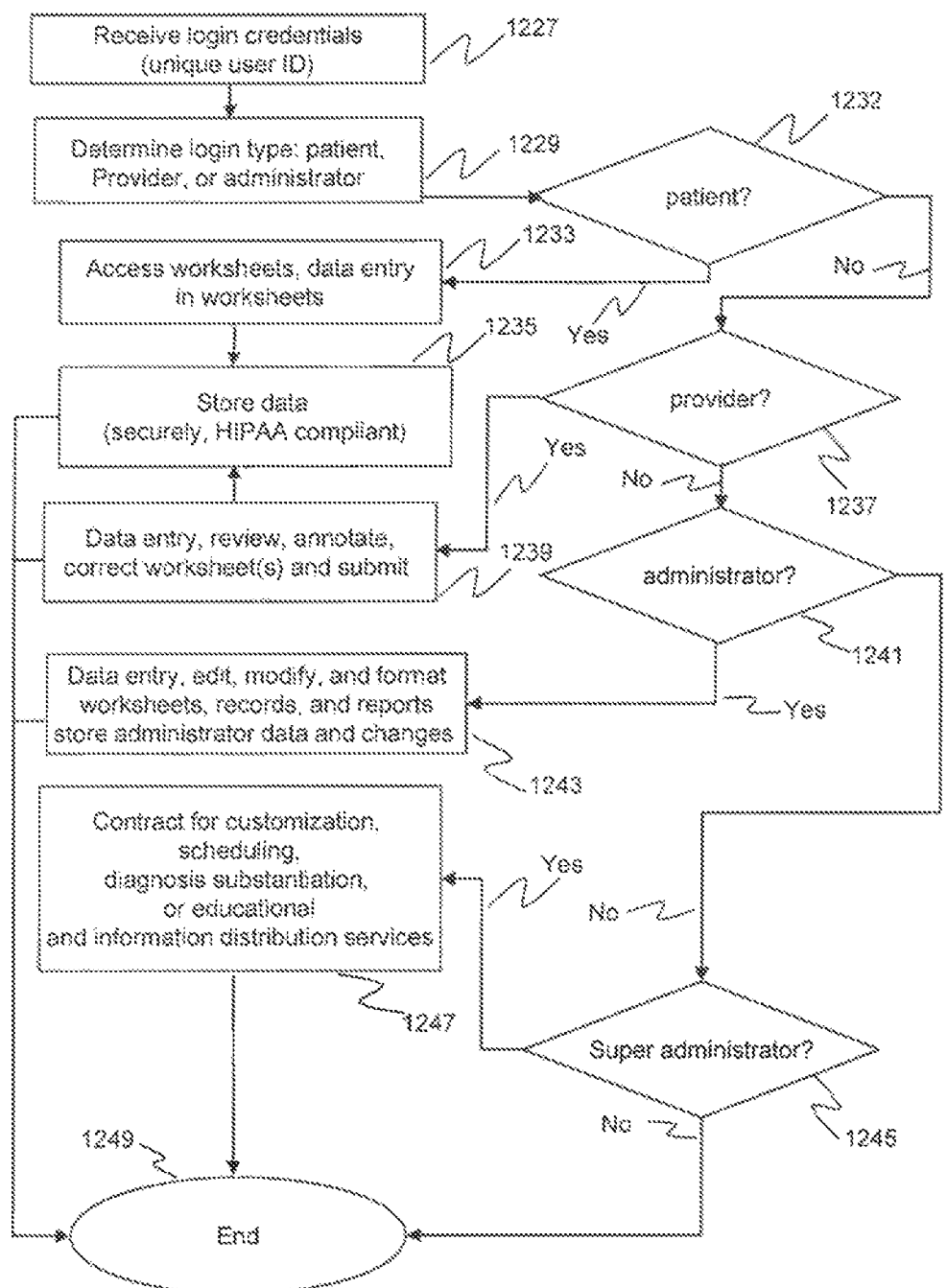
FIG. 12 is a flowchart illustrating steps by which a user is authenticated and medical information is accessed and edited, in accordance with an embodiment of the present invention.

FIG. 12 provides a method 1200 for enabling user registration, login processing, and worksheet processing using a computing device. FIG. 12 is described with continued reference to the embodiments illustrated in FIGS. 1-11. However, FIG. 12 is not limited to those embodiments.

Method 1200 begins in step 1227.

In step 1227, login credentials for a user are received. As shown in FIG. 12, step 1227 may comprise receiving a unique user ID. In embodiments, login credentials may be received from a mobile device, a terminal, a PC, or a server.

In one embodiment, step 1227 is performed by use of a registration module. The registration module may be invoked after a user, such as a patient 112 or provider 114 accesses a web server by directing an Internet browser to a web site and furnishes login credentials using log in screen. Features of the registration module are described below with reference to the exemplary login screen provided in FIG. 13. After login credentials are received, the method proceeds to step 1229.

In step 1229, a login type is determined. For example, a login of a patient 112, provider 114, or administrator 116 may be determined in this step. After the login type is determined, the method proceeds to step 1232.

In step 1232 if a determination was made that a registered patient 112 has logged in, control is passed to step 1233. If a determination is made that a patient 112 has not logged in, control is passed to step 1237.

In step 1233, privileges are granted to a patient 112 to access worksheets 124 and perform data entry in worksheets 124, in an embodiment, this step may comprise granting base privileges 1010 to the logged in patient 112 as described above with reference to FIG. 10. After the patient privileges are granted, the method proceeds to step 1235.

In step 1235, any data entry or changes performed in steps 1233 or 1239 are stored securely. According to an embodiment, this step may comprise storing the data in a HIPAA compliant, encrypted data store or database. In one embodiment, the entered or changed data may be encrypted prior to transmission to a server hosting a secure data store or database. After the patient-entered data is stored, control is passed to step 1249 where the process ends.

In step 1237, if a determination was made that a healthcare provider 114 has logged in, control is passed to step 1239. If a determination is made that a healthcare provider 114 has not logged in, control is passed to step 1241.

In step 1239, privileges are granted to a healthcare provider 114 to perform data entry, review, annotation and correction for worksheets 124 and exam worksheets 204, in this step, permissions are also granted to a provider 114 to enable submission of the worksheets as medical records 232. In an embodiment, step 1239 may comprise granting provider privileges 1020 to the logged in provider 114 as described above with reference to FIG. 10. Step 1239 further comprises receiving any data entry, annotation, and correction in worksheets from a logged in provider 114. After privileges are granted to a logged in provider and any provider data entry, annotation and correction has been completed, control is passed to back to step 1235 where any data entry, changes, or annotation performed by a provider 114 is securely stored.

In step 1241, if a determination was made that an administrator 116 has logged in, control is passed to step 1243. If a determination is made that an administrator 116 has not logged in, control is passed to step 1247.

In step 1243, privileges are granted to an administrator 116 to perform data entry, editing, modification, and formatting in worksheets 124, exam worksheets 204, medical records 232, and reports 206. In an embodiment, this step may comprise granting administrator privileges 1030 to the logged in administrator 116 as described above with reference to FIG. 10. Step 1243 further comprises receiving any data entry, modification, and formatting in worksheets from a logged in administrator 116. After privileges are granted to a logged in administrator and any administrator data entry, modification and formatting has been completed, the changes and data is securely stored and control is passed to step 1249.

In step 1245, if a determination was made that a super administrator has logged in, control is passed to step 1247. If a determination is made that a super administrator has not logged in, control is passed to step 1249.

In step 1247, privileges are granted to a super administrator to contract for customization, scheduling, diagnosis substantiation, or educational and information distribution services. In accordance with an embodiment of the invention, step 1247 may comprise granting super administrator privileges 1040 to the logged in administrator as described above with reference to FIG. 10. After the privileges are granted, a super administrator can subsequently contract for scheduling, diagnosis substantiation, or educational and information distribution services and then control is passed to step 1249 where the process ends.

Example Graphical User Interfaces

FIGS. 13-29 illustrate an exemplary GUI 1300 for provider login, patient searching, the prescription module 208, exam worksheets, and provider worksheets, in accordance with an embodiment of the invention.

FIGS. 13-29 depict a graphical user interface (GUI) within an exemplary website for displaying medical examination information, medical information, and reports. In an embodiment of the invention, login screen 110, secure web site 118, worksheets 124, exam worksheets 204, reports 206, modules 208, may include the exemplary interface illustrated in FIGS. 13-29. FIGS. 13-29 are described with continued reference to the embodiments illustrated in FIGS. 1-12. However, FIGS. 13-29 are not limited to those embodiments. Throughout FIGS. 13-29, displays are shown with various hyperlinks, command regions, tabs, buttons, checkboxes, and data entry fields, which are used to initiate action, invoke routines, enter data, view data, or invoke other functionality. For brevity, only the differences occurring within the figures, as compared to previous or subsequent ones of the figures, are described below.

FIGS. 13-29 illustrate an exemplary GUI 1300 for provider login, patient searching, the prescription module 208, exam worksheets, and provider worksheets, in accordance with an embodiment of the invention. In the example embodiment depicted in FIGS. 13-29, GUI 1300 is a web interface accessed via an Internet browser. Although in the exemplary embodiments depicted in FIGS. 13-29 the GUI is shown as an web interface running in a MICROSOFT™ Internet Explorer browser on a MICROSOFT™ WINDOWS™ operating system, it is understood that the GUI can be readily adapted to execute on a display of other client platforms and operating systems, a computer terminal, a display of mobile device, a display console of an application server, or other display of a computing device.

Figure 13:
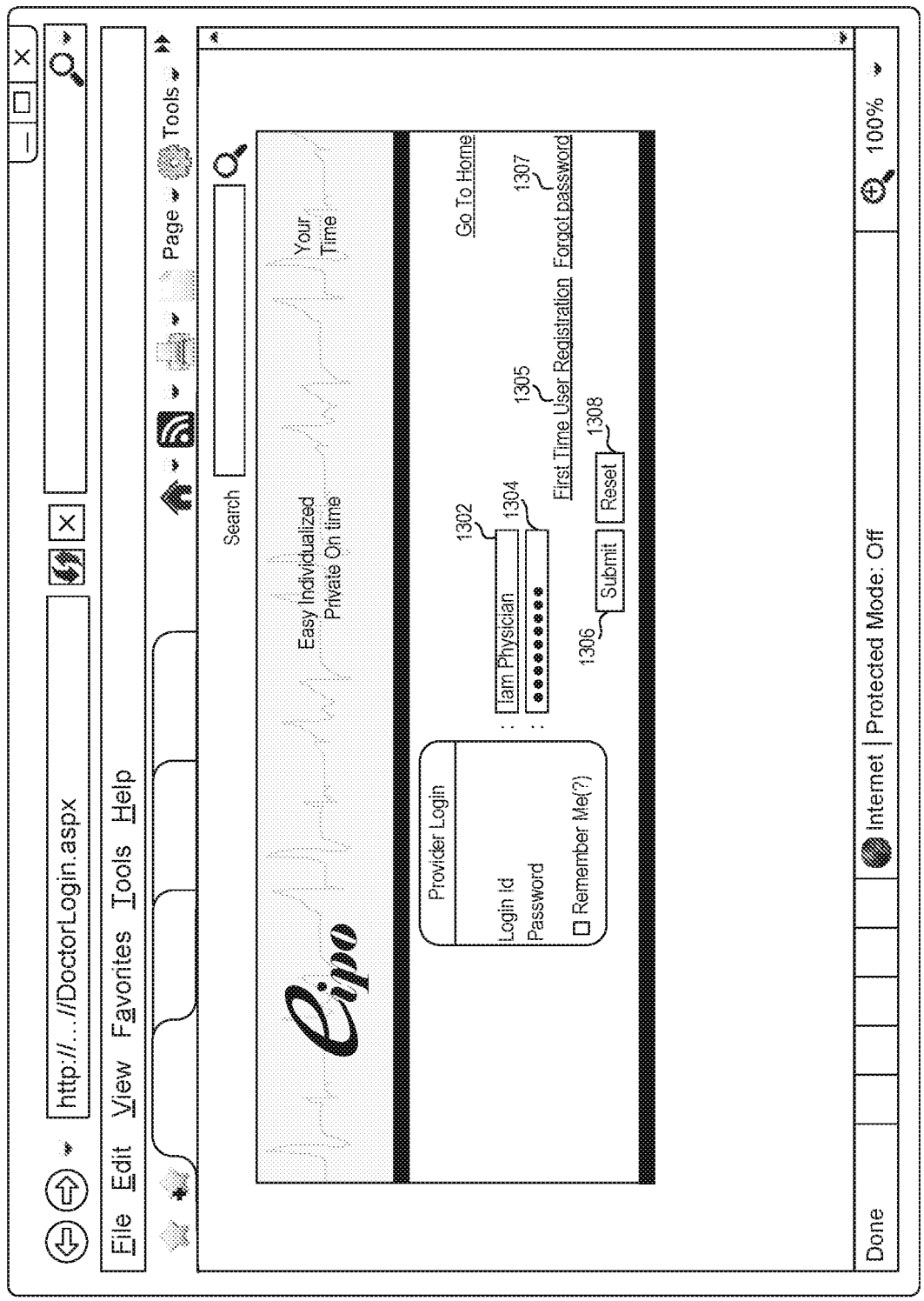

FIG. 13 illustrates a top-level web page interface 1300 that a provider may access at a PC, a client (such as a mobile client device), or a terminal in order to login. After logging in, a provider may access the patient searching, exam worksheet, and provider worksheet functionality described below with reference to FIGS. 14-29.

Figure 14:
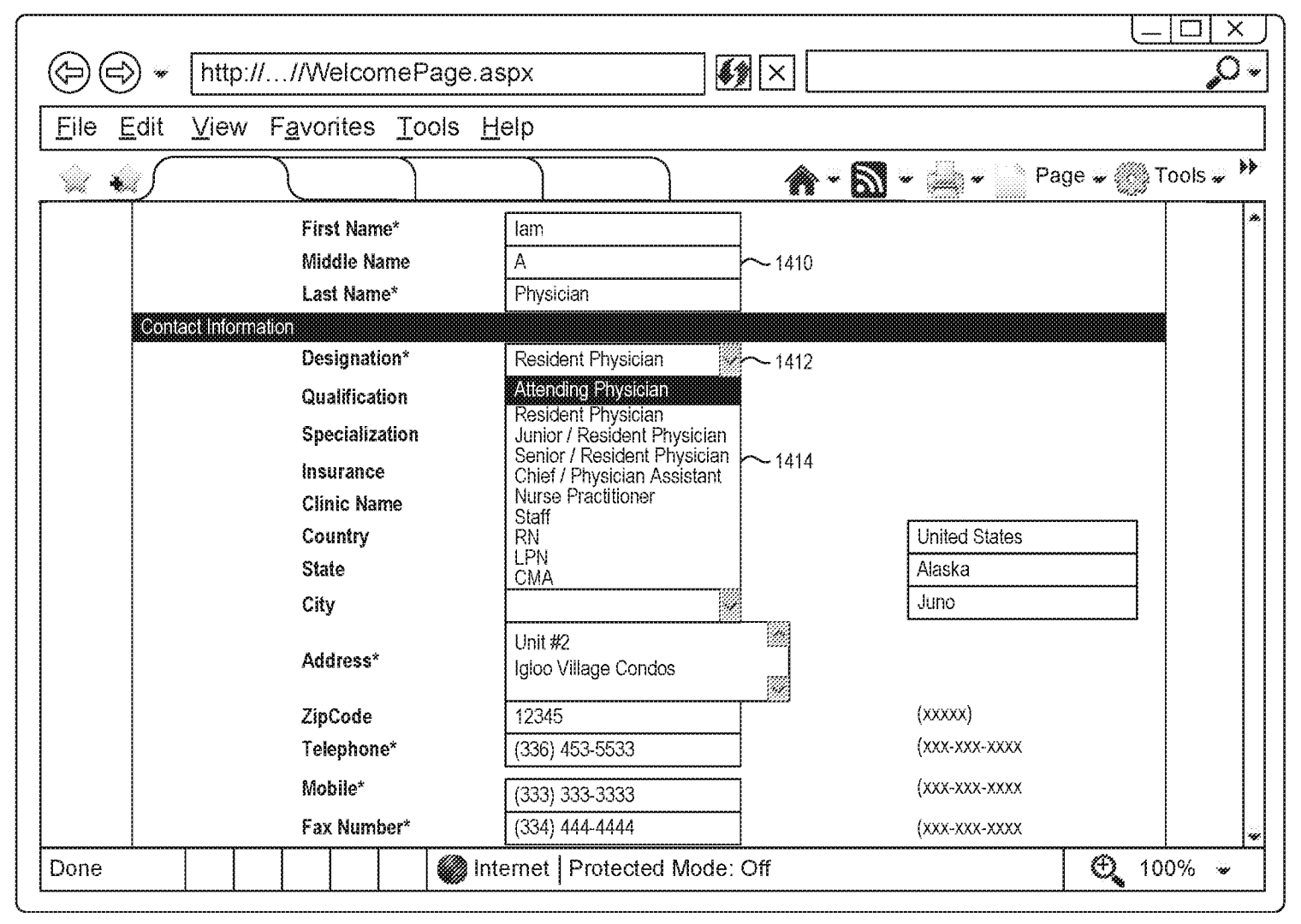

In the example embodiment depicted in FIG. 13, a provider, using an input device, may enter a login ID and password in login ID field 1302 and password field 1304 to login. By selecting one of hyperlinks 1305 or 1307, a new provider may register for the site and retrieve a forgotten password, respectively. For example, in an embodiment, by selecting hyperlink 1305, the provider registration interface depicted in FIG. 14 is launched. A provider may also select submit button 1306 to login using the login ID and password entered into login ID field 1302 and password field 1304. A provider may also select reset button 1308 to clear login ID field 1302 and password field 1304.

FIG. 14 depicts a provider registration interface. According to an embodiment of the invention, a provider, using an input device, may enter his/her name in name fields 1410. A provider, using an input device, can then select provider designation menu 1412 to display a drop-down menu 1414 listing types of providers.

Figure 15:
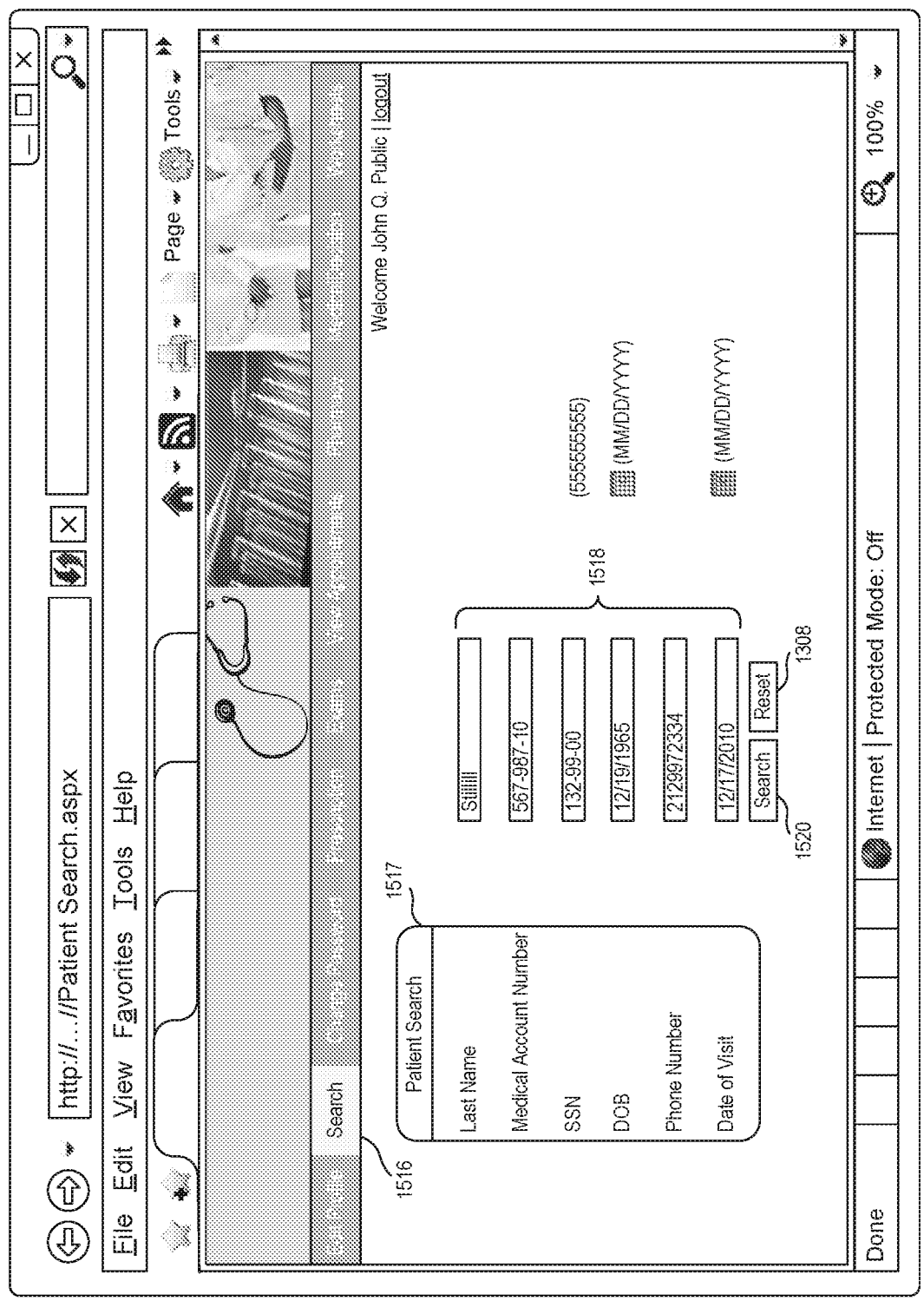

FIG. 15 illustrates a patient search tab 1516, in an embodiment, a provider may select patient search tab 1517 after selecting search tab 1516 using an input device in order to search for a patient. In the example embodiment depicted in FIG. 15, a provider may enter one or more patient search fields 1518, such as, but not limited to the patient's last name, medical account number, social security number (SSN), data of birth (DOB), phone number and/or date of visit. A provider may select search button 1520 to initiate a search for a patient using the data entered into patient search fields 1518. A provider may also select reset button 1308 to clear patient search fields 1518.

Figure 16:
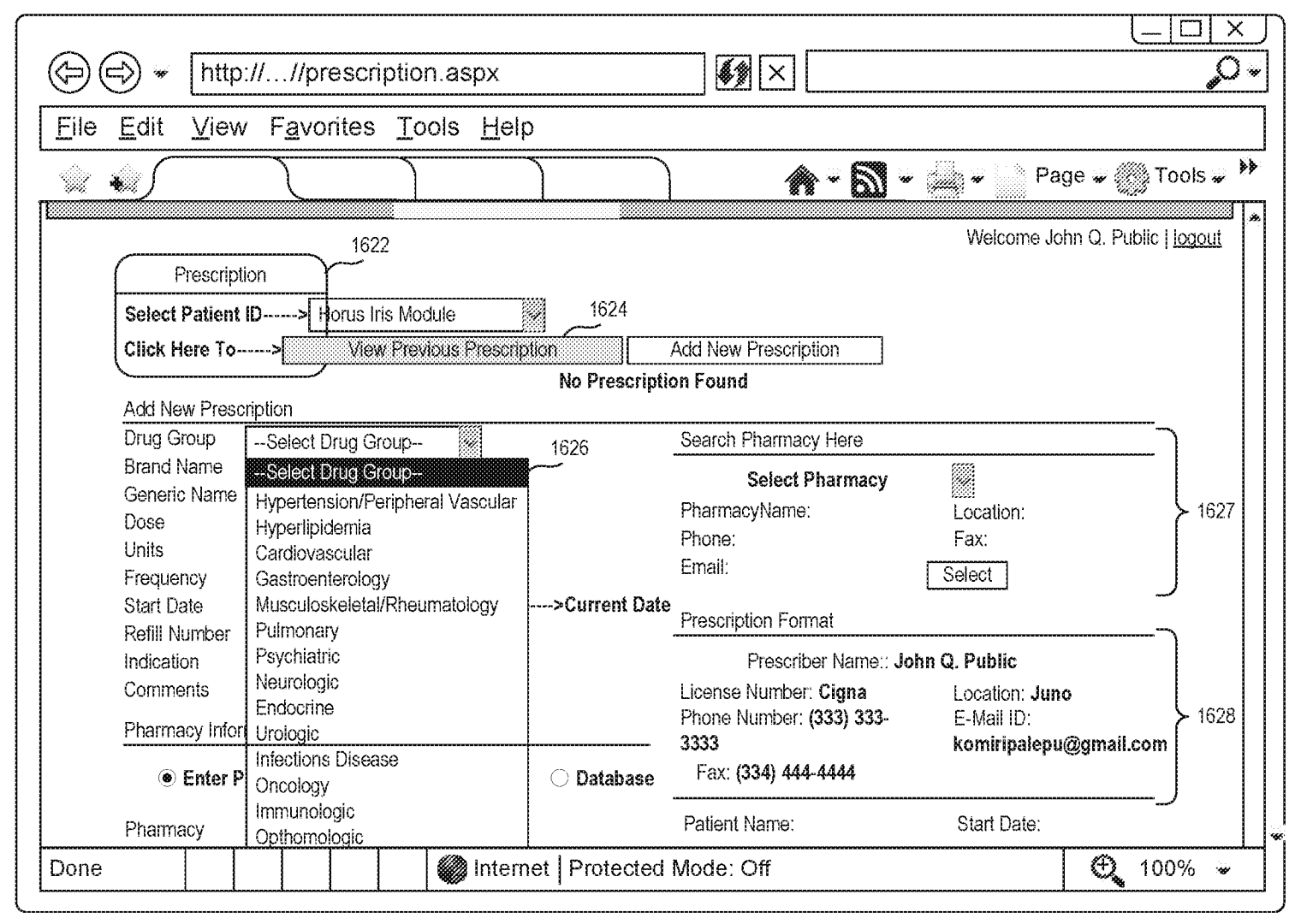
Figure 17:
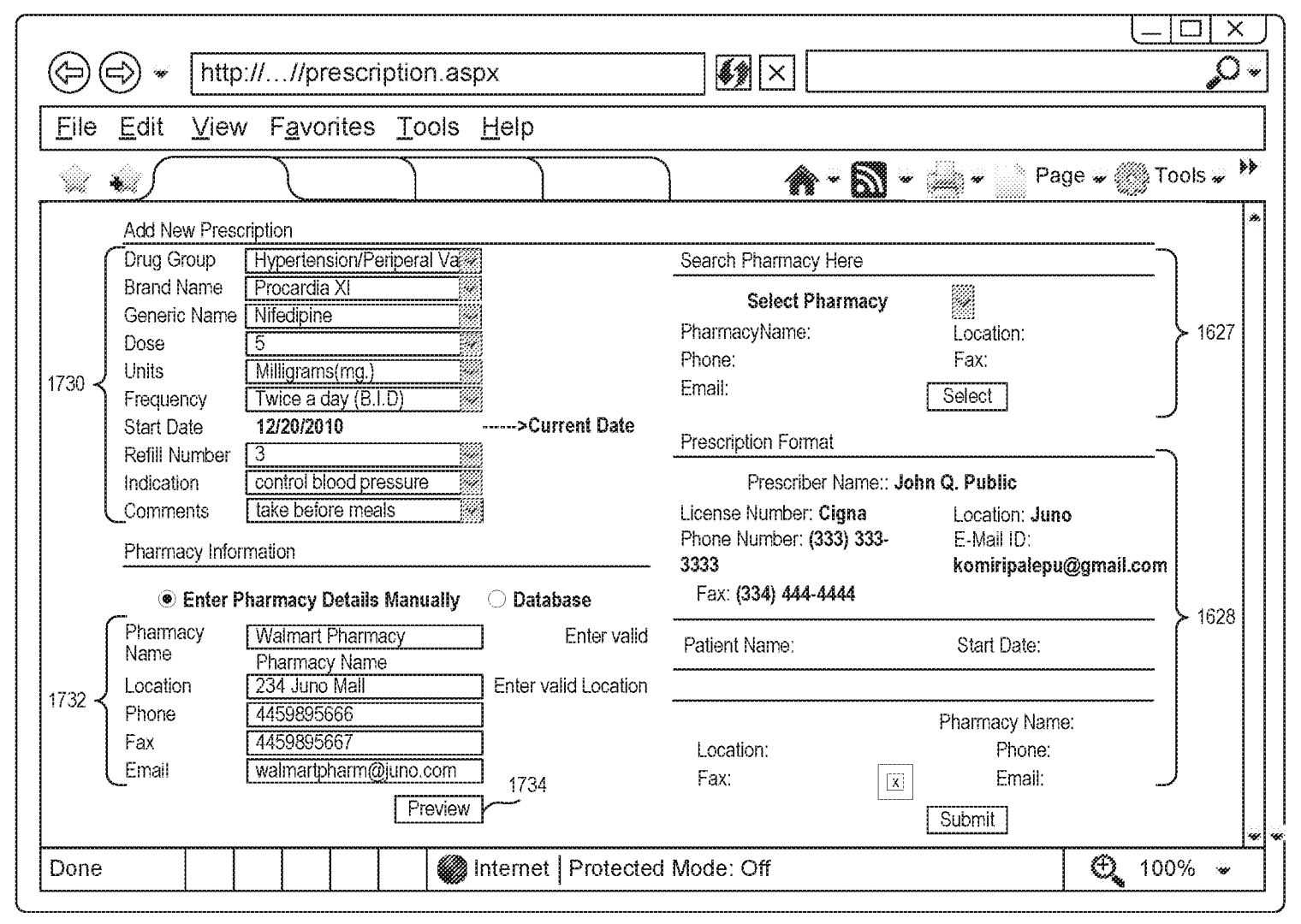

FIGS. 16 and 17 illustrate a GUI for viewing, entering, and editing prescription data. In an embodiment, the prescription data conveyed and entered in the GUI shown in FIGS. 16 and 17 is received from and communicated to the pharmacy/prescription module 208 discussed above with reference to FIGS. 2 and 3.

FIG. 16 depicts prescription tab 1622. In an embodiment, a provider may select prescription tab 1622 to invoke a prescription module 208. As shown in FIG. 16, pharmacy search fields 1627 can be entered to search for a pharmacy. By selecting, using an input device, view prescription button 1624, existing prescription fields 1628 for a previous prescription can be displayed. In the exemplary embodiment of FIG. 16, no previous prescription is found and selection of prescription drop down menu 1626 displays drug groups. According to an embodiment, the drugs groups are classified for use with the spectral array discussed above with reference to FIGS. 5 and 7-9.

FIG. 17 depicts an interface for displaying and editing drug and pharmacy details. In an embodiment, the pharmacy module 208 receives prescription fields 1730 and pharmacy fields 1732, which can be auto populated from a database accessible by the pharmacy module 208, or entered manually by a provider. As shown in FIG. 17, preview button 1734 can be selected to preview the new prescription based upon the prescription fields 1730.

FIGS. 18-29 depict interfaces for viewing, entering, and editing data associated with a medial exam within an exemplary GUI, in accordance with an embodiment of the present invention. In an embodiment, a user can select data fields and items shown in FIGS. 18-29 by hovering an input device (not shown) over tabs indicating general choices. As tabs are activated by hovering, expanded field choices are presented or opened. This process may extend for several "layers" of choices until a final choice is made by selecting, using an input device a worksheet 124 or an exam worksheet 204. According to an embodiment, this final choice causes a worksheet 124 in a specific module 208 to be displayed.

The descriptions of FIGS. 18-29 below describe the concepts of exam hierarchies, i.e., a general exam with its sub exams, a specialty exam also having its corresponding sub exams. However, FIGS. 18-29 simply demonstrate navigation and layout of some of the exam worksheets and their sequence does not imply a linear connectivity between the exams depicted.

In an embodiment, the exam data conveyed and entered in the GUI shown in FIGS. 18-29 can be used to populate worksheets 124 and exam worksheets 204 discussed above with reference to FIGS. 2-4 and 10.

Figure 18:
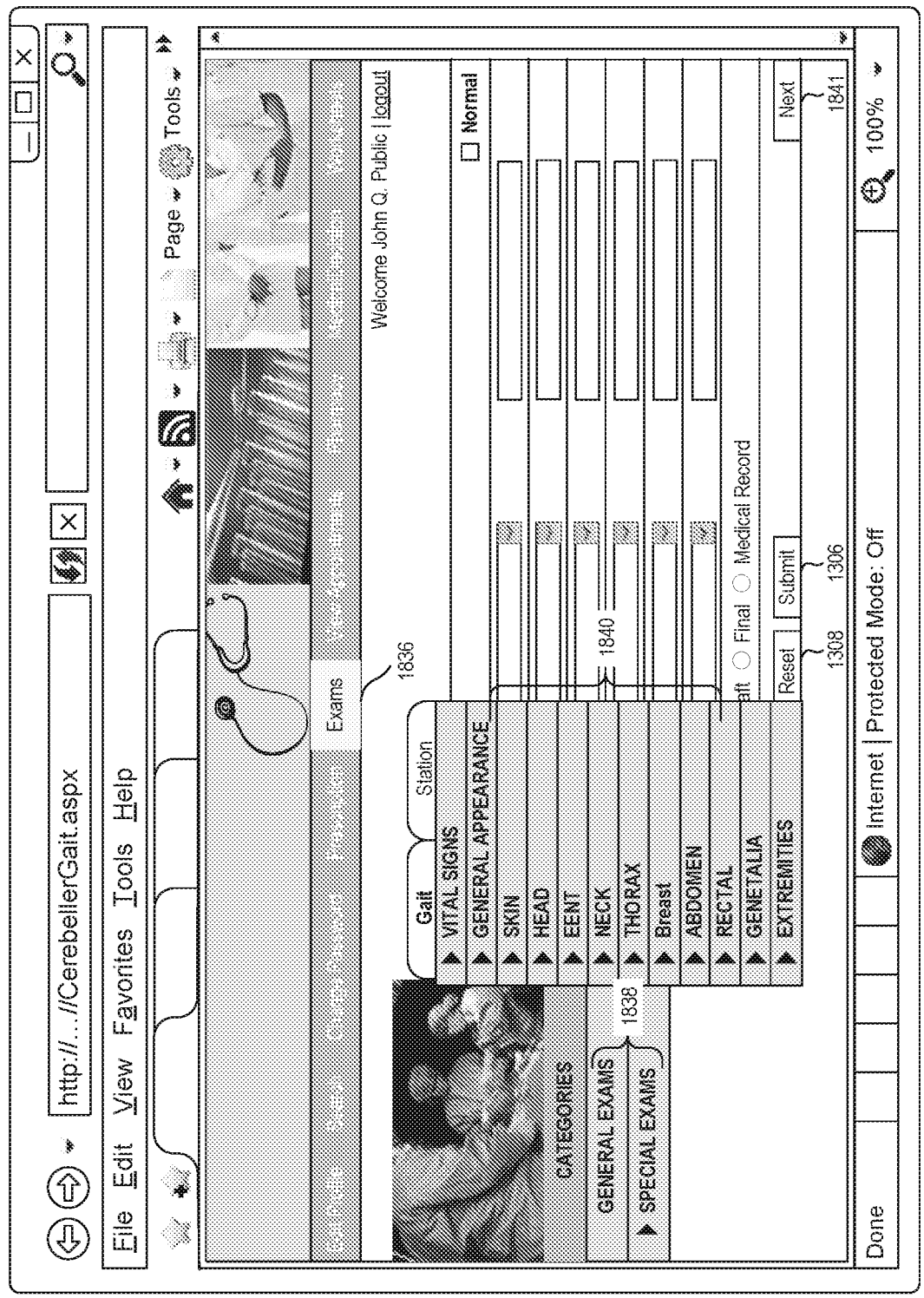

FIG. 18 depicts an interface for selecting exam options for a general exam, in accordance with an embodiment of the invention. By selecting, using an input device, exam tab 1836, a provider can select an exam category 1838. Once the special exam category 1838 is selected, in the embodiment of FIG. 18, special exam options 1840 are displayed. Once the exam category 1838 and exam options 1840 are selected, exam data fields described below with reference to FIGS. 19-26 can be entered. Once exam data fields have been entered, selection of submit button 1306 submits the selected data as a new exam. Alternatively, selection of reset button 1308 clears exam category 1838 and exam options 1840. By selecting, using an input device, Next button 1841, a provider can navigate to the vital signs interface described below with reference to FIG. 19.

Figure 19:
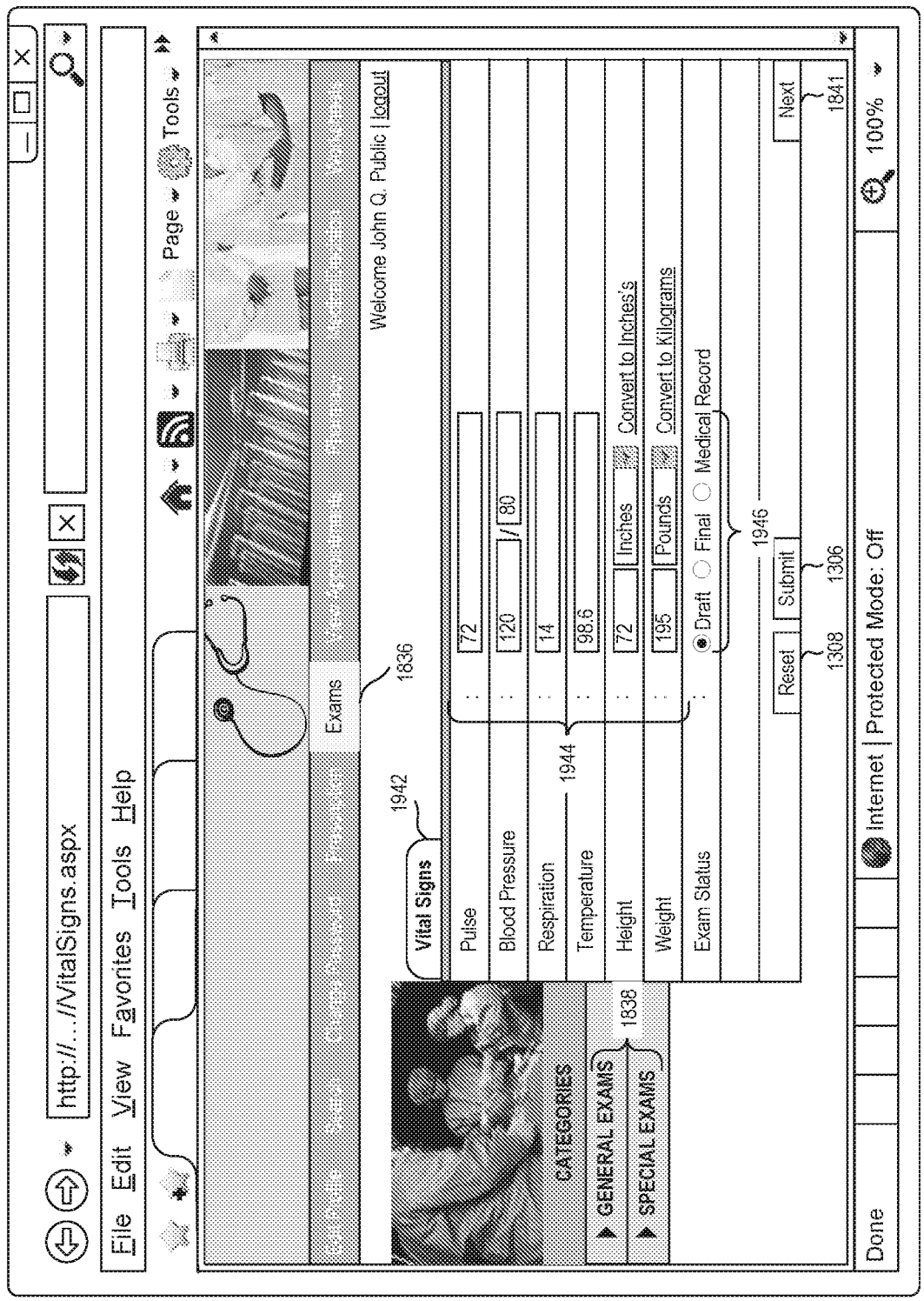

FIG. 19 depicts a vital signs interface accessible within exam tab 1836. As shown in FIG. 19, vital signs tab 1942 can be selected, using an input device, to enter vital sign fields 1944 into a medical record. As illustrated in FIG. 19, radio buttons 1946 can be selected to designate that vital sign fields 1944 are in draft or final form. Radio buttons 1946 can also be selected to add vital sign fields 1944 to a medical record. By selecting, using an input device, Next button 1841, a provider can navigate to the patient appearance interface described below with reference to FIG. 20.

Figure 20:
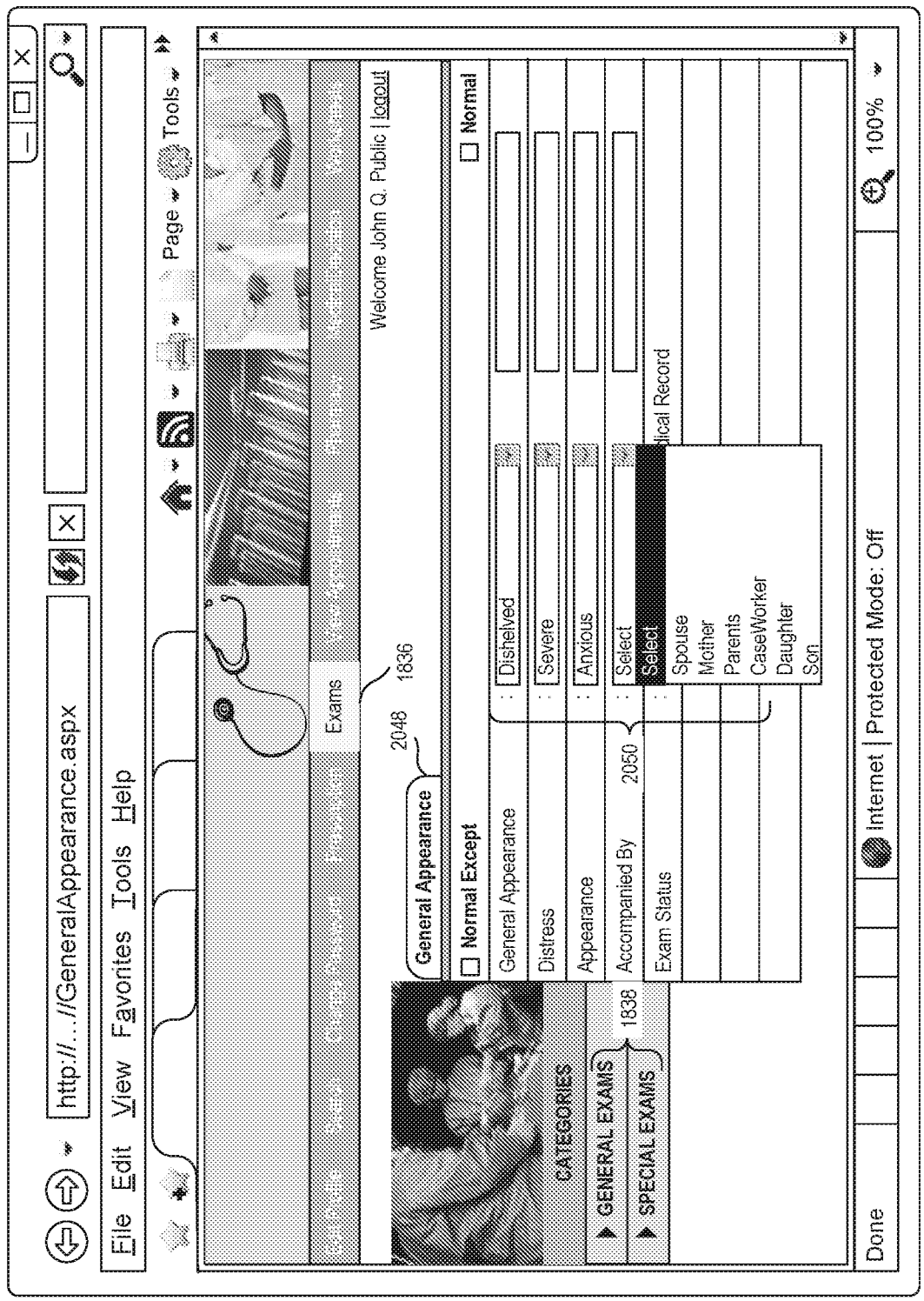

FIG. 20 illustrates a patient appearance interface accessible within exam tab 1836. As depicted in FIG. 20, a provider, using an in input device can select general appearance tab 2048 to select one or more patient appearance fields 2050. In the exemplary embodiment shown in FIG. 20, patient appearance fields 2050 can be entered as values from drop down menus. In an embodiment, the patient appearance fields 2050 may include, but are not limited to the patient appearance fields 2050 shown in FIG. 20. In the example provided in FIG. 20, a drop-down menu with values for the 'Accompanied By' data field is shown.

Figure 21:
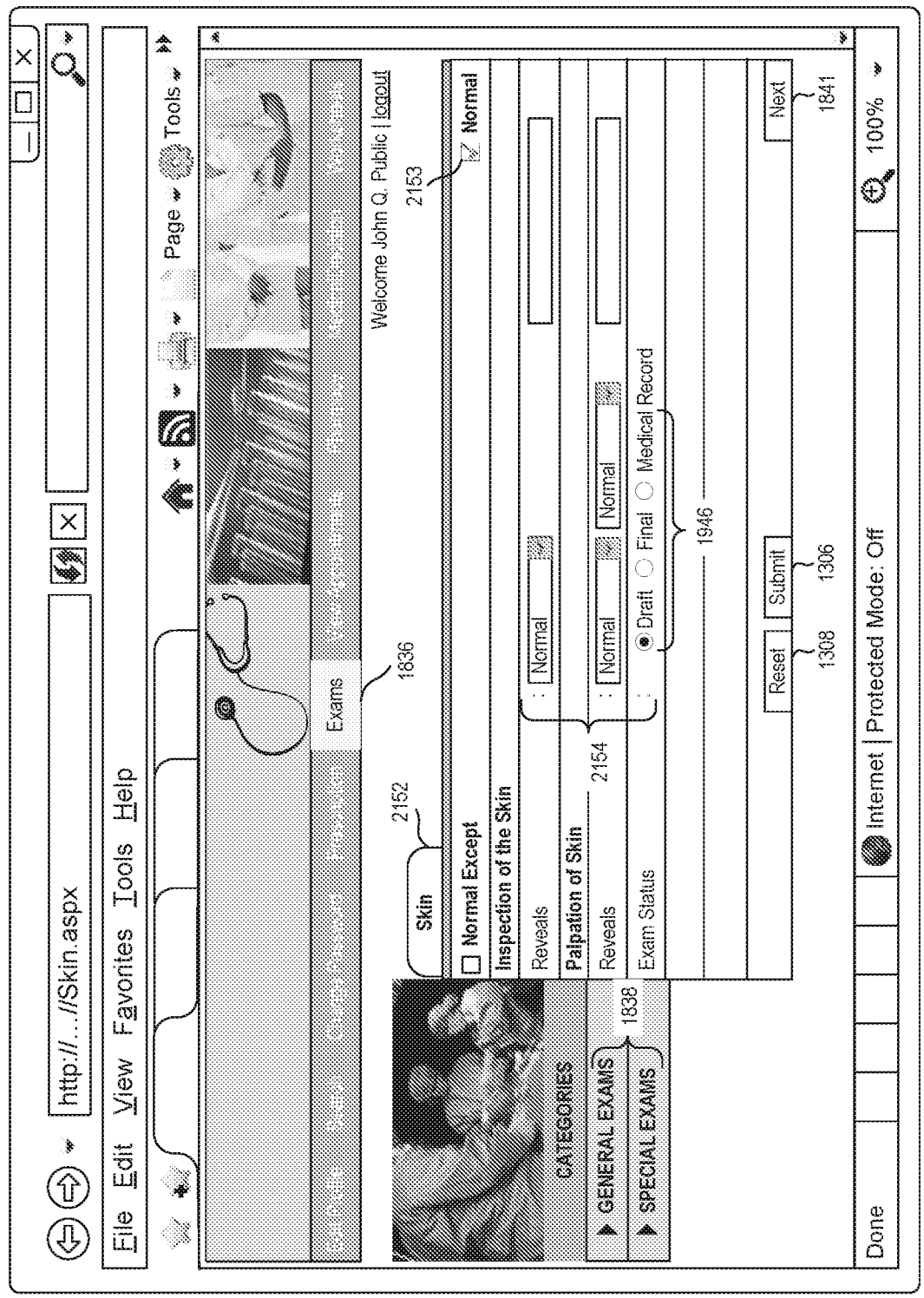

FIG. 21 illustrates a skin appearance interface within exam tab 1836. As shown in the exemplary embodiment of FIG. 20, by selecting, using an input device, normal check box 2153, skin appearance fields 2154 are populated with default 'normal' values. By selecting, using an input device, Next button 1841, a provider can navigate to the ears, eyes, nose, throat (EENT) interface described below with reference to FIG. 22.

Figure 22:
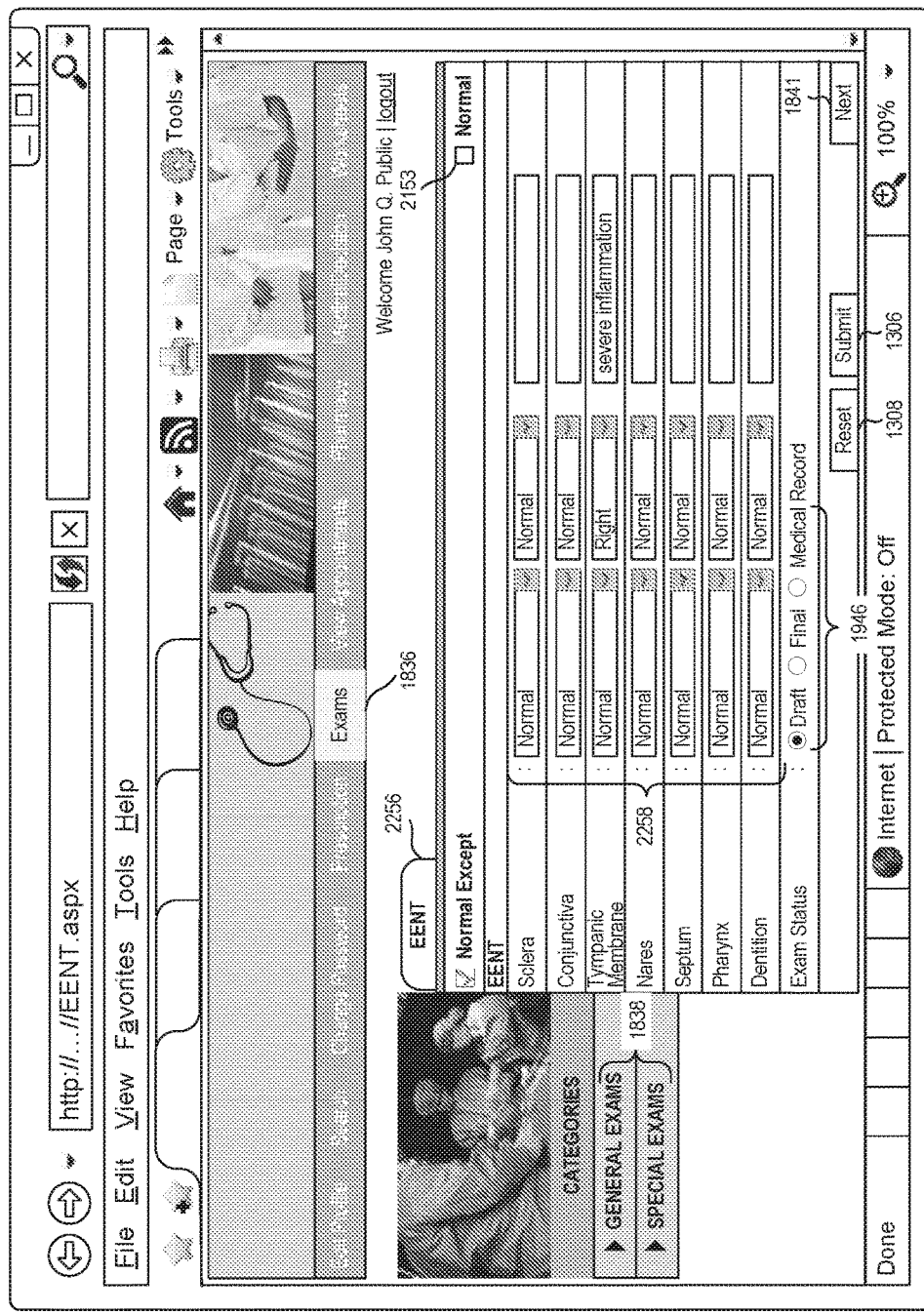

FIG. 22 depicts an ears, eyes, nose, throat (EENT) interface accessed within exam tab 1836. By selecting, using an input device, EENT tab 2256, a provider can enter EENT fields 2258. As shown in FIG. 22, even when EENT fields 2258 are otherwise 'normal,' a provider can edit individual EENT fields 2258 (i.e., tympanic membrane change) and enter textual comments for edited fields. In an embodiment, the EENT fields 2258 may include, but are not limited to the EENT fields 2258 shown in FIG. 22. By selecting, using an input device, Next button 1841, a provider can navigate to the thorax interface described below with reference to FIG. 23.

Figure 23:
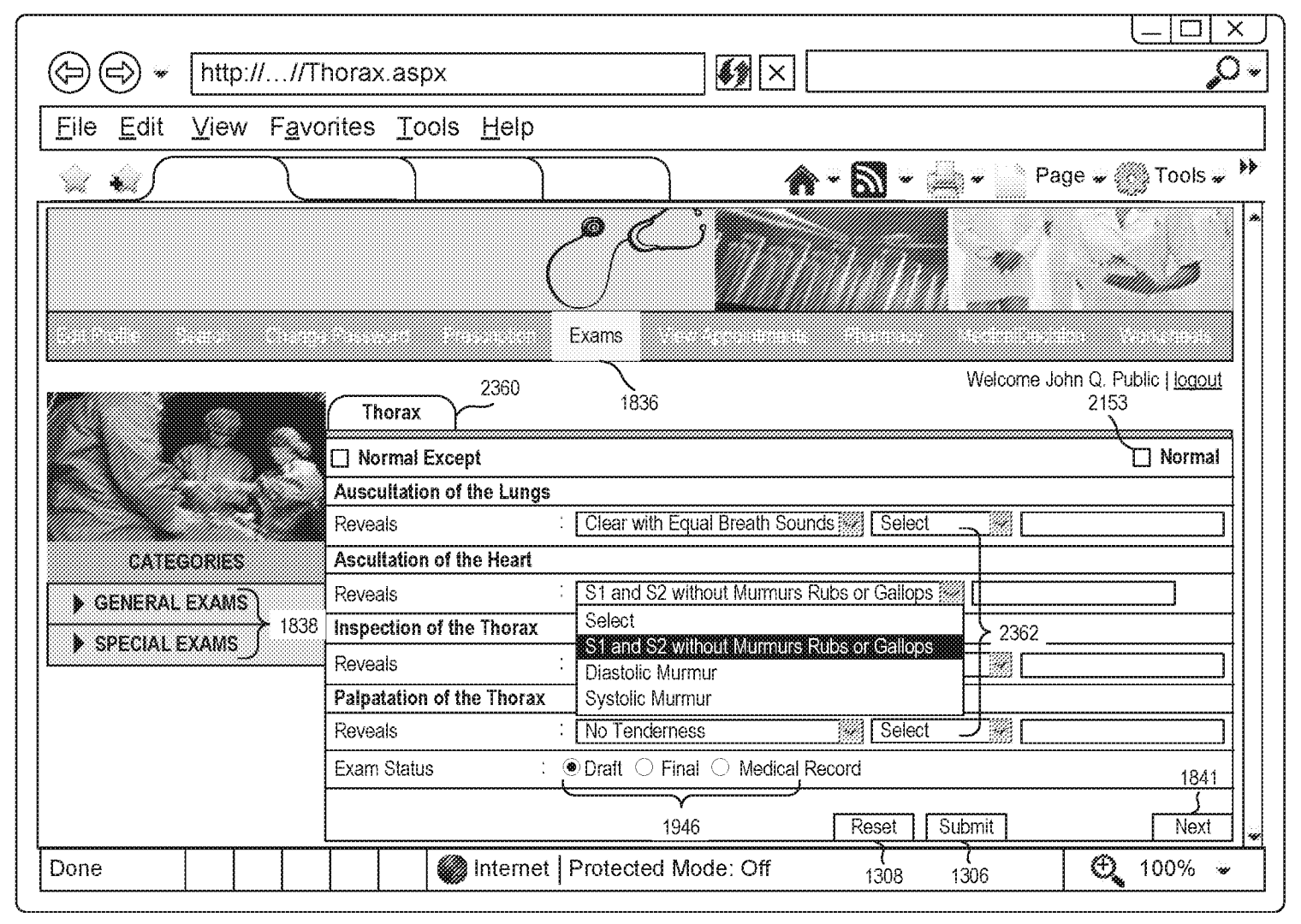
Figure 24:
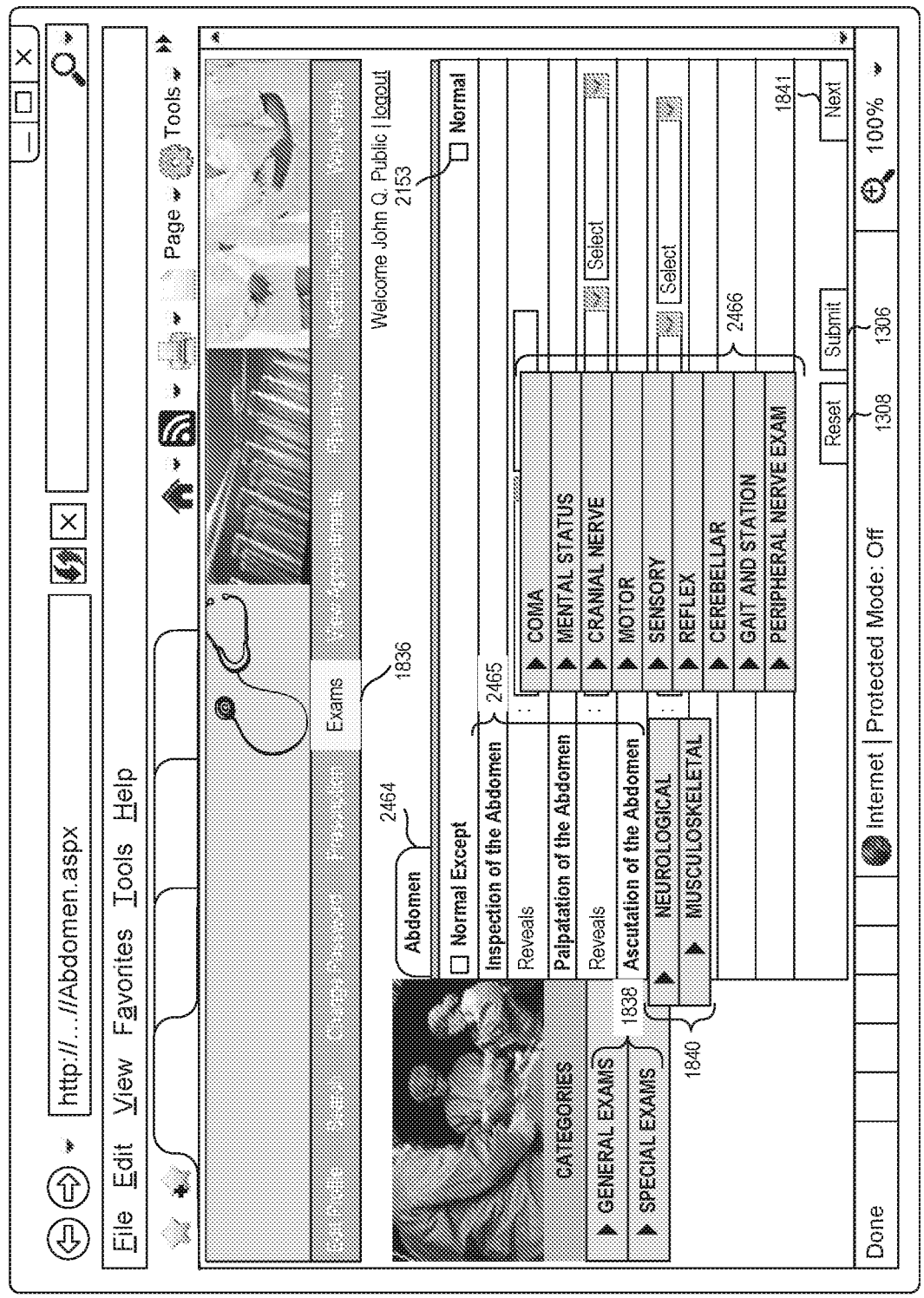

FIG. 23 depicts a thorax interface accessible within exam tab 1836. By selecting, using an input device, thorax tab 2360, a provider can enter thorax fields 2362. As shown in the exemplary embodiment of FIG. 23, there are drop down menu options for each thorax field 2362 so that a provider can note any abnormal values. As further illustrated in FIG. 23, some of thorax fields 2362 can be coded for reports. According to an embodiment, the thorax fields 2362 may include, but are not limited to the thorax fields 2362 shown in FIG. 23. By selecting, using an input device, Next button 1841, a provider can navigate to the specialty exam interface described below with reference to FIG. 24. According to an embodiment of the invention, at any time, user can "hover" to select a specialty or for that matter, any exam. It is simply displayed on this web page that the specialty exam "hover to select" feature occurs with the thorax exam in the background, it is understood that the specialty exam has nothing to do with the abdominal exam, and the illustrations of FIGS. 23 and 24 are provided to show the hovering capability and not to give the appearance that the specialty exam—neurological—is reached or navigated to from the abdominal exam. In the example of FIG. 23, the thorax interface is just the next exam worksheet image being selected and until the hover function becomes a click is selected by a user), the previous exam worksheet image, stays on the screen.

FIG. 24 provides an example specialty exam interface accessible within exam tab 1836. By selecting, using an input device, abdominal tab 2464, a provider can enter abdominal fields 2465. In accordance with an embodiment, the abdominal fields 2465 may include, but are not limited to the abdominal fields 2465 shown in FIG. 24. By selecting, using an input device, Next button 1841, a provider can navigate to the thorax interface described below with reference to FIG. 25. Also, once an exam category 1838 is selected, in the embodiment of FIG. 24, neurological exam options 1840 are displayed. Once the exam category 1838 and exam options 1840 are selected, sub exams 2466 are displayed. These specialty exams are sub exams of the general exam and a user can jump at any time to specialty exams, and in turn navigate to sub exams of the specialty exams.

Figure 25:
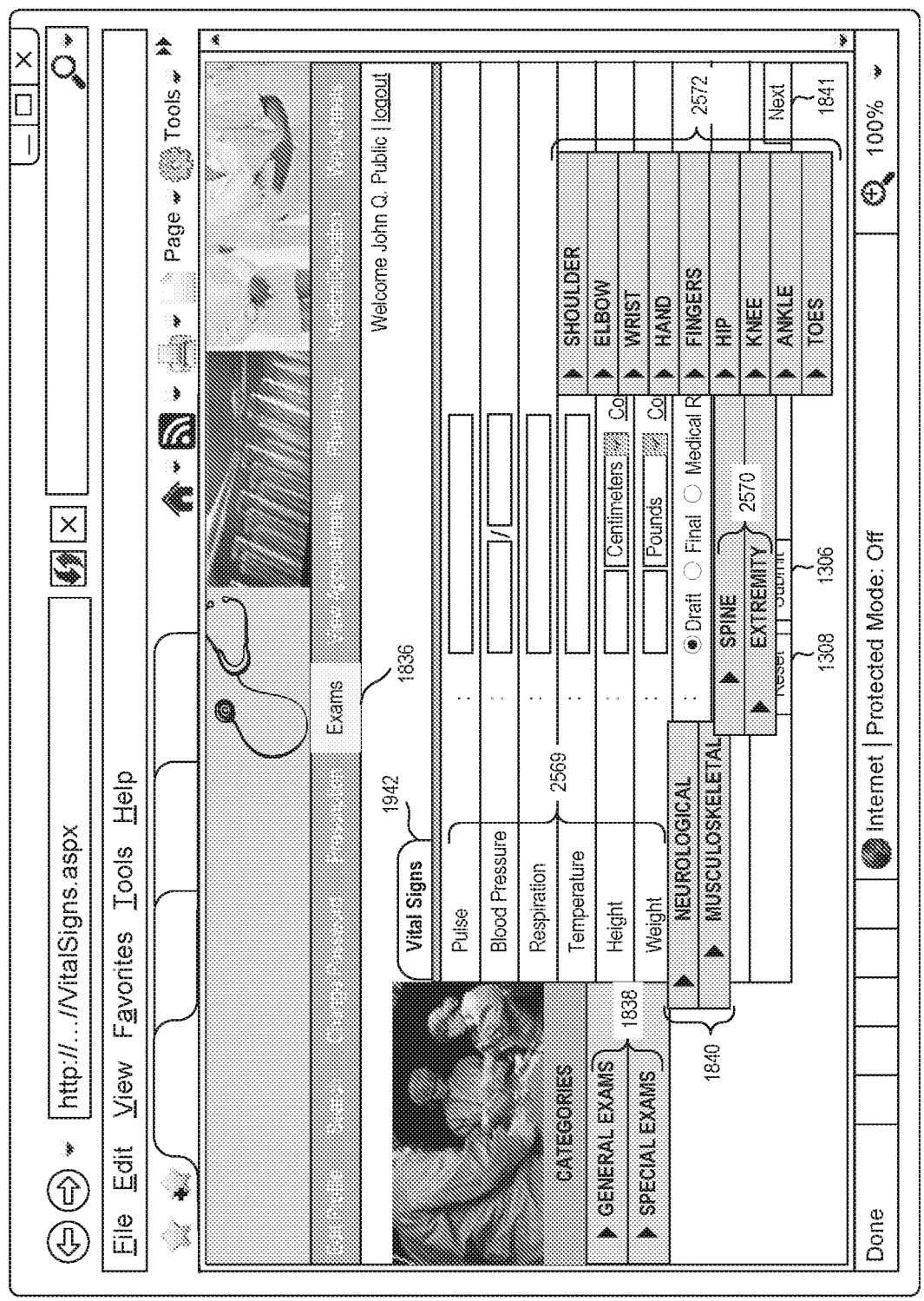

FIG. 25 depicts a musculoskeletal specialty exam interface within exam tab 1836. By selecting, using an input device, vital signs tab 2568, a provider can enter vital sign fields 2569. In the example of FIG. 25, a user is in a specialty exam and can revert or navigate back to a sub exam of the general exam—vital signs. The interface shown allows a user to do all sub exams of an exam category in sequence. Additionally, once an exam category 1838 and exam option 1840 is selected, in the embodiment shown in FIG. 25, musculoskeletal exam options 2570 are displayed. In an embodiment, once the exam category 1838, an exam option 1840, and musculoskeletal exam options 2570 are selected, 'fly away' menus 2572 for sub exams are displayed.

Figure 26:
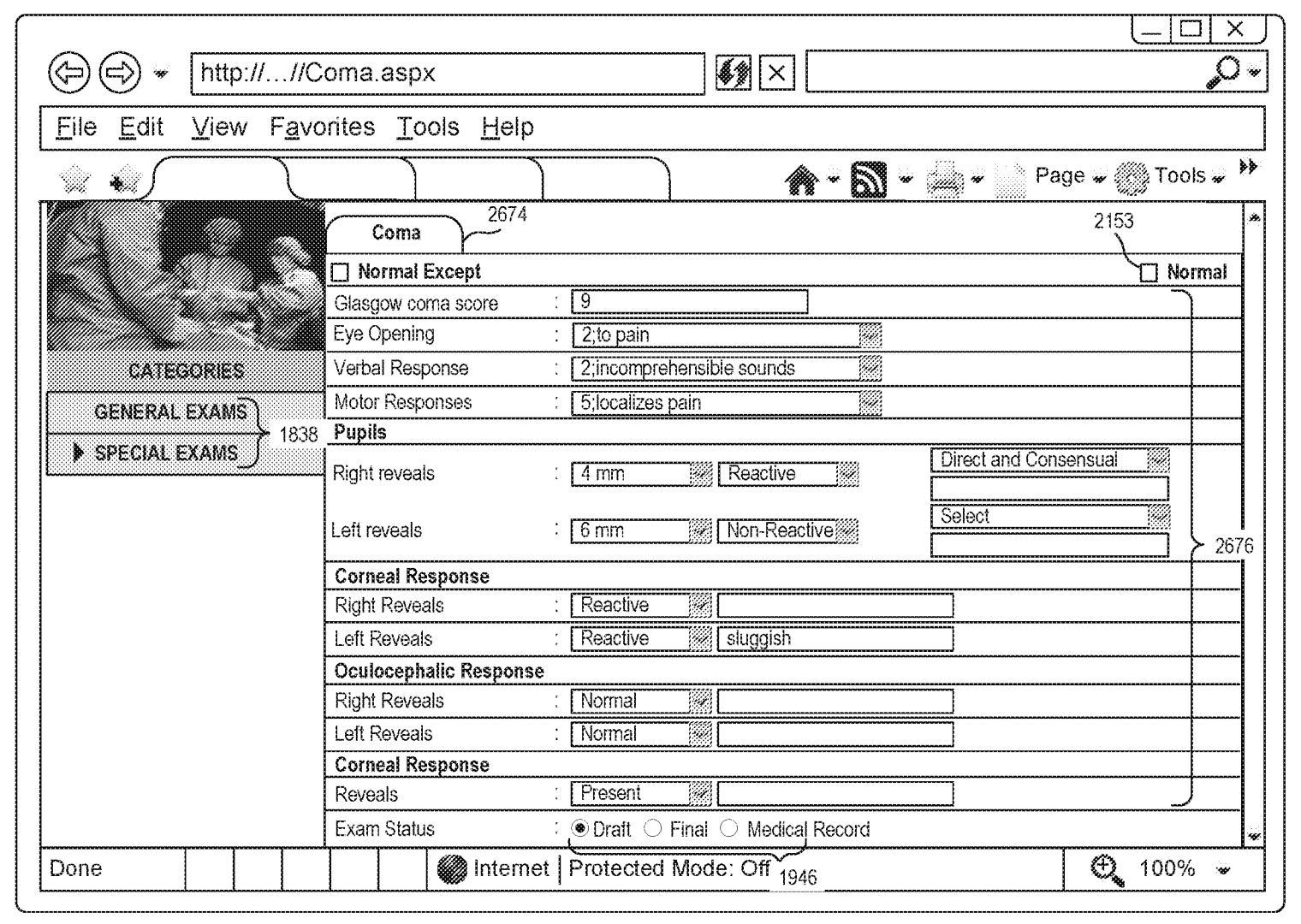
Figure 27:
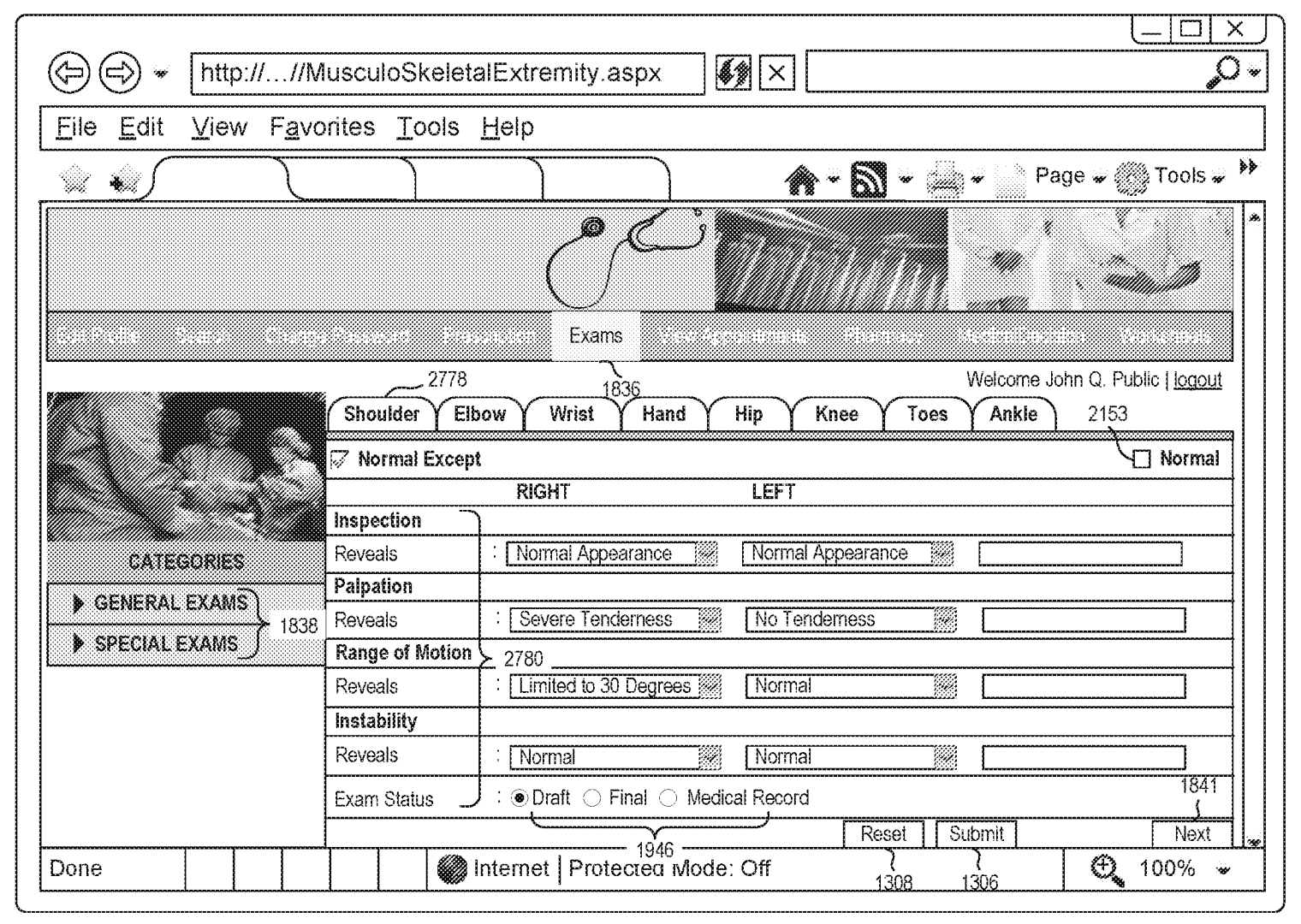

FIGS. 26 and 27 depict an example sub exam interface for a neurological specialty exam. By selecting, using an input device, coma tab 2674, a provider can enter coma fields 2676. As shown in FIG. 27, by selecting shoulder tab 2778, a provider can enter and edit shoulder fields 2780.

Figure 28:
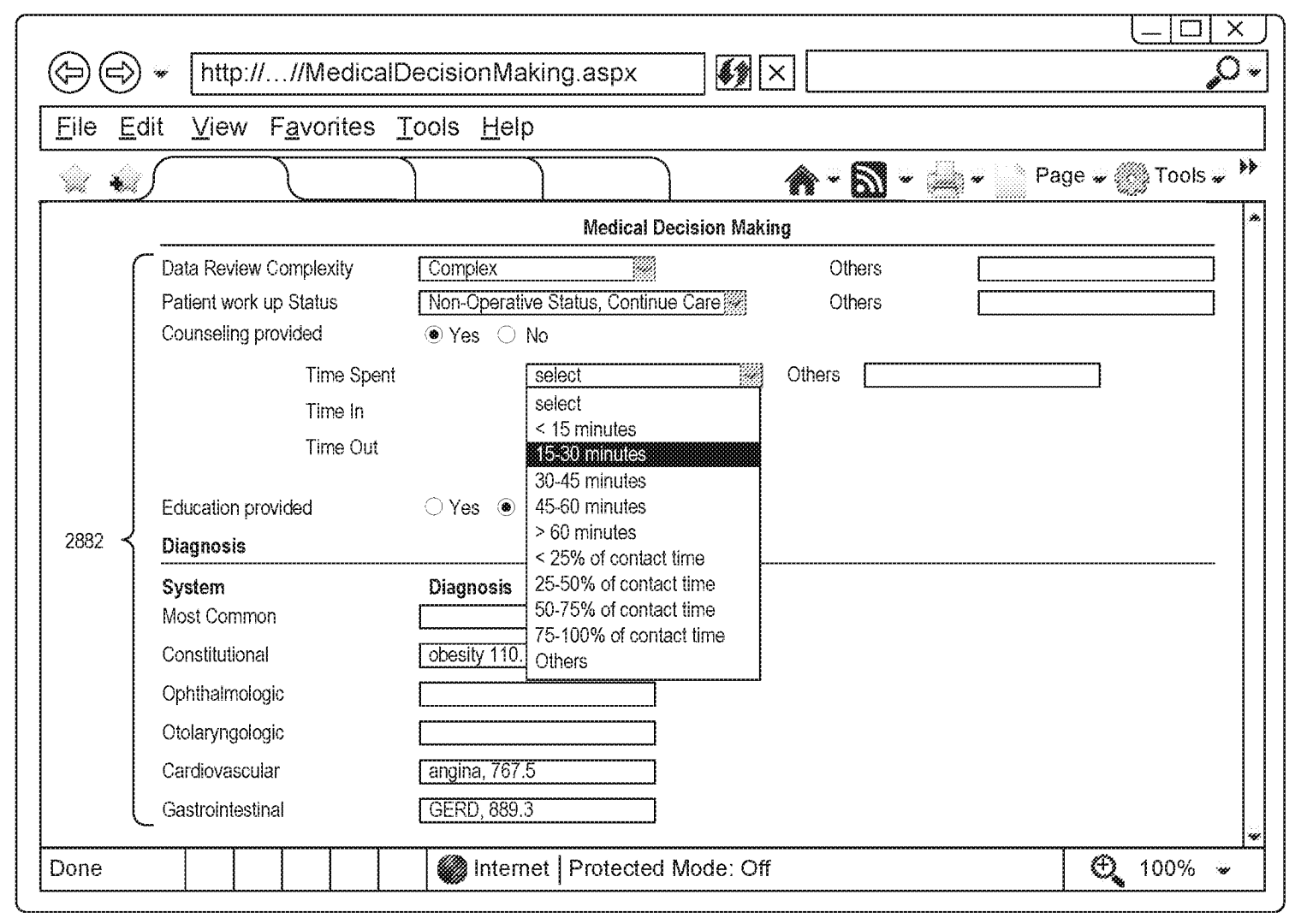
Figure 29:
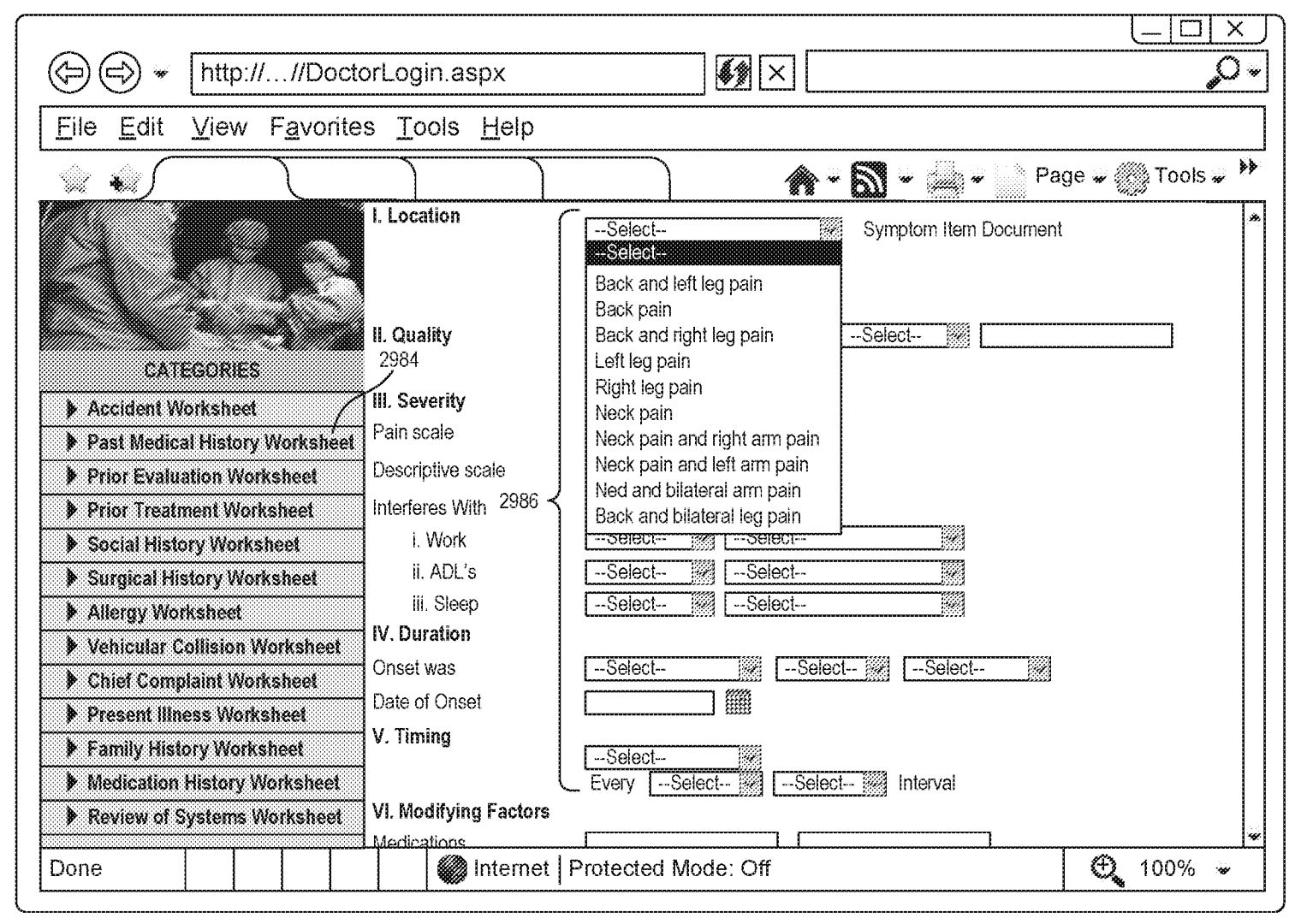

FIGS. 28 and 29 depict a provider worksheet interface, in accordance with an embodiment of the invention. As shown in FIG. 28, a medical decision making interface displays a plurality medical decision fields 2882, in the example embodiment of FIG. 28, one or more of medical decision fields 2882 can be entered via drop-down menus pre-populated with data choices. As shown in FIG. 29, by using the provider worksheet interface, a provider can select past medical history worksheet hyperlink 2984 to view a past medical history fields 2986. As further depicted in FIG. 29, a provider, using an input device, can also select a variety of other provider worksheets 2988 so that the provider can work directly with patient to complete the worksheets.

Example Computer System Implementation

Various aspects of the present invention can be implemented by software, firmware, hardware, or a combination thereof. FIG. 30 illustrates an example computer system 3000 in which the present invention, or portions thereof, can be implemented as computer-readable code. For example, the method illustrated by the flowchart 1200 of FIG. 12 can be implemented in system 3000. Personal health information systems 100-300 of FIGS. 1-3 can also be implemented in system 3000. Various embodiments of the invention are described in terms of this example computer system 3000. After reading this description, it will become apparent to a person skilled in the relevant art how to implement the invention using other computer systems and/or computer architectures.

Computer system 3000 includes one or more processors, such as processor 3004. Processor 3004 can be a special purpose or a general-purpose processor. Processor 3004 is connected to a communication infrastructure 3006 (for example, a bus, or network).

Computer system 3000 also includes a main memory 3008, preferably random access memory (RAM), and may also include a secondary memory 3010. Secondary memory 3010 may include, for example, a hard disk drive 3012, a removable storage drive 3014, flash memory, a memory stick, and/or any similar non-volatile storage mechanism. Removable storage drive 3014 may comprise a floppy disk drive, a magnetic tape drive, an optical disk drive, a flash memory, or the like. The removable storage drive 3014 reads from and/or writes to a removable storage unit 3018 in a well-known manner. Removable storage unit 3018 may comprise a floppy disk, magnetic tape, optical disk, etc. which is read by and written to by removable storage drive 3014. As will be appreciated by persons skilled in the relevant art(s), removable storage unit 3018 includes a non-transitory computer readable storage medium having stored therein computer software and/or data.

In alternative implementations, secondary memory 3010 may include other similar means for allowing computer programs or other instructions to be loaded into computer system 3000. Such means may include, for example, a removable storage unit 3022 and an interface 3020. Examples of such means may include a program cartridge and cartridge interface (such as that found in video game devices), a removable memory chip (such as an EPROM, or PROM) and associated socket, and other removable storage units 3022 and interfaces 3020 which allow software and data to be transferred from the removable storage unit 3022 to computer system 3000.

Computer system 3000 may also include a communications interface 3024. Communications interface 3024 allows software and data to be transferred between computer system 3000 and external devices. Communications interface 3024 may include a modem, a network interface (such as an Ethernet card), a communications port, a PCMCIA slot and card, or the like. Software and data transferred via communications interface 3024 are in the form of signals, which may be electronic, electromagnetic, optical, or other signals capable of being received by communications interface 3024. These signals are provided to communications interface 3024 via a communications path 3026. Communications path 3026 carries signals and may be implemented using wire or cable, fiber optics, a phone line, a cellular phone link, an RF link or other communications channels.

Computer system 3000 may additionally include computer display 3030. According to an embodiment, computer display 3030, in conjunction with display interface 3002, can be used to display the spectral arrays depicted in FIGS. 5 and 7-9 and the user interfaces illustrated in FIGS. 13-29. Computer display 3030 may also be used as an interactive interface (not shown) displayed via a display interface 3002 on a mobile client device.

In this document, the terms "computer program medium," "non-transitory computer readable medium," and "computer usable medium" are used to generally refer to media such as removable storage unit 3018, removable storage unit 3022, and a hard disk installed in hard disk drive 3012. Signals carried over communications path 3026 can also embody the logic described herein. Computer program medium and computer usable medium can also refer to memories, such as main memory 3008 and secondary memory 3010, which can be memory semiconductors (e.g. DRAMs, etc.). These computer program products are means for providing software to computer system 3000.

Computer programs (also called computer control logic) are stored in main memory 3008 and/or secondary memory 3010. Computer programs may also be received via communications interface 3024. Such computer programs, when executed, enable computer system 3000 to implement the present invention as discussed herein. In particular, the computer programs, when executed, enable processor 3004 to implement the processes of the present invention, such as the steps in the methods illustrated by method 1200 of FIG. 12 and systems 100-300 of FIGS. 1-3 discussed above. For example, the modules 208 described above with reference to FIGS. 2, 3, 16 and 17 can be implemented as computer programs. Accordingly, such computer programs represent controllers of the computer system 3000. Where the invention is implemented using software, the software may be stored in a computer program product and loaded into computer system 3000 using removable storage drive 3014, interface 3020, hard drive 3012, or communications interface 3024.

The invention is also directed to computer program products comprising software stored on any computer useable medium. Such software, when executed in one or more data processing device, causes a data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

Conclusion

While various embodiments of the present invention have been described above, it should be understood that they have been presented by way of example only, and not limitation. It will be understood by those skilled in the relevant art(s) that various changes in form and details may be made therein without departing from the spirit and scope of the invention as defined in the appended claims. It should be understood that the invention is not limited to these examples. The invention is applicable to any elements operating as described herein. Accordingly, the breadth and scope of the present invention should not be limited by any of the above-described exemplary embodiments, but should be defined only in accordance with the following claims and their equivalents.

What is claimed is:

1. A method for processing medical data comprising:
    displaying, in a client interface, an interactive worksheet comprising a plurality of questions associated with a registered patient;
    receiving responses to the plurality of questions;
    displaying, in the client interface, the received responses, wherein the client interface is configured to receive edits to the received responses;
    sending the received responses to a provider;
    displaying, in a provider interface, the received responses as a grid, wherein the provider interface is configured to receive annotations and edits to at least one of the received responses;
    converting, by a processor, the received responses into a medical record for the registered patient; and
    displaying the medical record as a spectral array including plotting medical data corresponding to a plurality of body systems associated with the registered patient that is weighted according to a level of objectivity or intervention using color, symbol, and timeline elements to represent the registered patient's medical history, wherein the spectral array comprises links to further information or data.

2. The method of claim 1, wherein the provider is one or more of a personal health record (PHR) vendor, a healthcare provider, a pharmacy, a hospital, a medical clinic, an assisted living facility, a government organization, or an insurance company.

3. The method of claim 1, further comprising displaying, in the client interface, a drop down box for respective ones of the plurality of questions having a predefined list of responses.

4. The method of claim 3, further comprising:
    determining that there can be another response to the question;
    displaying, in the client interface, after receiving a previous response to the question, an option dialog box comprising a prompt for a subsequent response to the question; and
    repeating the determining and the displaying until the determining determines that there is not another response to the question.

5. The method of claim 4, wherein the interactive worksheet is one or more of: an exam worksheet, an allergy worksheet, a chief complaint worksheets, a history of present illness worksheet, an accident worksheet, a collision worksheet, a medication worksheet, a past medical history worksheet, a surgery worksheet, a family history worksheet, a social history worksheet, and a review of systems worksheet.

6. The method of claim 1, further comprising displaying, in the client interface, a plurality of data fields related to a question in response to receiving a response to the question.

7. The method of claim 1, wherein the client interface can be used to grant permission to a third party to view the received responses.

8. The method of claim 7, wherein the permission is granted for a duration of time.

9. A system for conveying personal health information, comprising:
 a server computer having a processor and a non-transitory computer-readable medium having instructions stored thereon, the instructions comprising:
  an authentication routine to cause the server computer to receive login credentials;
  a determination routine to cause the server computer to determine, based upon the login credentials, a login type;
  a reception routine to cause the server computer to present an interactive interface for receiving worksheet data, wherein the presented interface and the worksheet data are based in part upon the login type; and
  a conversion routine to convert at least a portion of the worksheet data into a medical record, the medical record being represented as a spectral array comprising a plurality of body systems associated with a registered patient that is weighted according to a level of objectivity or intervention using color, symbol, and timeline elements to represent the registered patient's medical history, wherein the spectral array comprises links to further information or data.

10. The system of claim 9, wherein the instructions further comprise:
 a storage routine to cause the server computer to store the worksheet data and the medical record in a secure database;
 a selection routine to cause the server computer to select a subset of the worksheet data stored in the secure database; and
 an access routine to cause the server computer to grant a designated entity access to the subset of the worksheet data stored in the secure database.

11. The system of claim 9, wherein the login type is one or more of a patient, provider, administrator, or super administrator.

12. The system of claim 11, wherein the provider is one or more of a personal health record (PHR) vendor, a healthcare provider, a pharmacy, a hospital, a medical clinic, an assisted living facility, a government organization, or an insurance company.

13. The system of claim 11, wherein in response to determining that the login type is the patient, the reception routine receives data entry via one or more worksheets.

14. The system of claim 11, wherein in response to determining that the login type is the provider, the reception routine causes the server computer to present an exam worksheet, and wherein the reception routine enables the provider to perform exam worksheet data operations comprising:
 review;
 annotation;
 correction;
 data entry;
 finalization; and
 declaration of the exam worksheet as an addition to the medical record, wherein the declaration invokes a conversion routine to convert data from the exam worksheet into the medical record.

15. The system of claim 11, wherein in response to determining that the login type is the administrator, the reception routine enables a patient to perform worksheet data operations comprising:
 editing;
 modification;
 formatting;
 data entry;
 review;
 annotation; and
 correction.

16. The system of claim 10, wherein the storage routine causes the server computer to store the medical record in a HIPAA-compliant secure database.

17. An apparatus comprising a non-transitory computer-readable medium having stored thereon, computer-executable instructions that, if executed by a computing device, cause the computing device to convey personal health information by a method comprising:
 receiving login credentials;
 determining, based upon the login credentials, a login type;
 presenting an interactive interface for receiving worksheet data, wherein the presented interactive interface and the worksheet data are based in part upon the login type;
 converting at least a portion of the worksheet data into a medical record;
 displaying the medical record as a spectral array including plotting medical data corresponding to a plurality of body systems associated with the registered patient that is weighted according to a level of objectivity or intervention using color, symbol, and timeline elements to represent the registered patient's medical history, wherein the spectral array comprises links to further information or data; and
 granting a designated entity access to at least a subset of the worksheet data or the medical record.

18. The apparatus of claim 17, wherein the apparatus is a mobile device having wireless communications capabilities.

19. A computer implemented method for conveying personal health information comprising:
 receiving, at a computing device, login credentials;
 determining, by the computing device, based upon the login credentials, a login type;
 presenting, on a display of the computing device, an interactive interface for receiving and annotating worksheet data, wherein the presented interactive interface and the worksheet data are based in part upon the login type;
 converting, by the computing device, at least a portion of the annotated worksheet data into a medical record;
 displaying the medical record as a spectral array including plotting medical data corresponding to a plurality of body systems associated with the registered patient that is weighted according to a level of objectivity or intervention using color, symbol, and timeline elements to represent the registered patient's medical history, wherein the spectral array comprises links to further information or data;
 storing, in a secure database, the worksheet data and the converted medical record; and
 transmitting the medical record to a designated entity.

20. The computer implemented method of claim 19, wherein the storing further comprises encrypting the worksheet data and the converted medical record.

21. The computer implemented method of claim 19, wherein the transmitting further comprises encrypting the medical record prior to transmitting the medical record.

22. The method of claim 1, wherein the converting comprises mapping the received responses to the plurality of body systems, the mapping comprising associating the received responses with weighted data values and associating the weighted data values with the plurality of body systems.

23. The method of claim 22, wherein the weighted data values comprise subjective data received from the registered patient or historical medical data associated with the registered patient.

24. The method of claim 22, wherein the displaying further includes using icons that are associated with the plurality of body systems.

25. The method of claim 1, wherein the displaying further includes representing the weighted data values according to a timeline that depicts an occurrence of a medical examination.

26. The method of claim 1, wherein the weighted data values are weighted using a numeric range according to a severity criterion or a level of significance of a symptom.

27. The method of claim 1:
wherein the spectral array further comprises body system specific color coding and icons to depict symptom severity;
wherein the spectral array is a snapshot of the client's known medical history for each of the plurality of body systems; and
wherein the weighted data values comprise at least subjective complaint data values, physical exam data values, which are weighted more than the subjective complaint data values, laboratory testing data values, which are weighted more than the physical exam data values, and surgery data values, which are weighted more than the laboratory testing data values.

28. The system of claim 9:
wherein the spectral array further comprises body system specific color coding and icons to depict symptom severity;
wherein the spectral array is a snapshot of the client's known medical history for each of the plurality of body systems; and
wherein the weighted data values comprise at least subjective complaint data values, physical exam data values, which are weighted more than the subjective complaint data values, laboratory testing data values, which are weighted more than the physical exam data values, and surgery data values, which are weighted more than the laboratory testing data values.

* * * * *

UNITED STATES PATENT AND TRADEMARK OFFICE
CERTIFICATE OF CORRECTION

PATENT NO. : 10,467,699 B2  
APPLICATION NO. : 13/094443  
DATED : November 5, 2019  
INVENTOR(S) : Amundson Page 1 of 2

It is certified that error appears in the above-identified patent and that said Letters Patent is hereby corrected as shown below:

In the Specification

In Column 1, Line 26, delete "patients" and insert -- patient's --, therefor.

In Column 5, Line 16, delete "arts)" and insert -- art(s) --, therefor.

In Column 5, Line 26, delete "Wherein" and insert -- wherein --, therefor.

In Column 6, Line 23, delete "example embodiment" and insert -- "an example embodiment," --, therefor.

In Column 7, Line 6, delete "client," and insert -- client. --, therefor.

In Column 11, Line 51, delete "122" and insert -- 122 to --, therefor.

In Column 15, Line 29, delete "410" and insert -- 410 may --, therefor.

In Column 15, Line 50, delete "an billable" and insert -- all billable --, therefor.

In Column 17, Line 37, delete "user" and insert -- user (i.e., --, therefor.

In Column 17, Line 64, delete "an be" and insert -- can be --, therefor.

In Column 18, Line 39, delete ""4,"" and insert -- "4." --, therefor.

In Column 19, Line 26, delete "hack" and insert -- back --, therefor.

In Column 20, Line 28, delete "user, in" and insert -- user. In --, therefor.

In Column 22, Line 26, delete "Windows" and insert -- windows --, therefor.

Signed and Sealed this  
Third Day of March, 2020

Andrei Iancu  
*Director of the United States Patent and Trademark Office*

CERTIFICATE OF CORRECTION (continued)
U.S. Pat. No. 10,467,699 B2

In Column 23, Line 62, delete "information, in" and insert -- information. In --, therefor.

In Column 25, Line 40, delete "124, in" and insert -- 124. In --, therefor.

In Column 25, Line 58, delete "204, in" and insert -- 204. In --, therefor.

In Column 27, Line 28, delete "1516, in" and insert -- 1516. In --, therefor.

In Column 27, Line 67, delete "medial" and insert -- medical --, therefor.

In Column 29, Lines 26-27, delete "background, it" and insert -- background. It --, therefor.

In Column 29, Line 34, delete "click" and insert -- click (i.e., --, therefor.

In Column 30, Line 7, delete "2882, in" and insert -- 2882. In --, therefor.